United States Patent
Truffert et al.

(10) Patent No.: US 9,994,604 B2
(45) Date of Patent: Jun. 12, 2018

(54) PYRAZOLOTRIAZOLYL NUCLEOSIDE ANALOGUES AND OLIGONUCLEOTIDES COMPRISING THEM

(71) Applicant: Bio-Lab Ltd., Jerusalem (IL)

(72) Inventors: Jean-Christophe Truffert, Saint-Prest (FR); Myriam Lefoix, Le Bardon (FR); Jean Hildesheim, Modiin-Macabim-Reut (IL); Tirtsa Kleinman, Jerusalem (IL)

(73) Assignee: Bio-Lab Ltd., Jerusalem (IL)

( * ) Notice: Subject to any disclaimer, the term of this patent is extended or adjusted under 35 U.S.C. 154(b) by 198 days.

(21) Appl. No.: 14/403,580

(22) PCT Filed: May 30, 2013

(86) PCT No.: PCT/IL2013/050461
§ 371 (c)(1),
(2) Date: Nov. 25, 2014

(87) PCT Pub. No.: WO2013/179289
PCT Pub. Date: Dec. 5, 2013

(65) Prior Publication Data
US 2015/0141490 A1    May 21, 2015

Related U.S. Application Data

(60) Provisional application No. 61/653,528, filed on May 31, 2012.

(51) Int. Cl.
| | |
|---|---|
| C12N 15/11 | (2006.01) |
| A01N 43/04 | (2006.01) |
| A61K 31/70 | (2006.01) |
| C07H 21/02 | (2006.01) |
| C07H 21/04 | (2006.01) |
| C07H 19/04 | (2006.01) |
| C07H 19/20 | (2006.01) |
| C12N 15/00 | (2006.01) |
| C12N 5/00 | (2006.01) |
| C12N 5/02 | (2006.01) |
| C07H 7/06 | (2006.01) |
| C07D 487/04 | (2006.01) |
| C12N 15/113 | (2010.01) |

(52) U.S. Cl.
CPC ............ C07H 7/06 (2013.01); C07D 487/04 (2013.01); C12N 15/113 (2013.01); C12N 2310/333 (2013.01); C12N 2310/336 (2013.01); C12N 2310/352 (2013.01)

(58) Field of Classification Search
CPC ...... C07H 7/06; C07D 487/04; C12N 15/113; C12N 2310/336; C12N 2310/333; C12N 2310/352
See application file for complete search history.

(56) References Cited

U.S. PATENT DOCUMENTS

| | | | |
|---|---|---|---|
| 5,652,099 A | 7/1997 | Conrad | |
| 5,763,167 A * | 6/1998 | Conrad | C07H 19/04 435/6.16 |
| 2004/0063658 A1* | 4/2004 | Roberts | C07H 19/052 514/45 |
| 2005/0074799 A1 | 4/2005 | Kennedy et al. | |
| 2006/0106019 A1 | 5/2006 | Bernard | |
| 2010/0093991 A1 | 4/2010 | Chand et al. | |
| 2012/0077814 A1 | 3/2012 | Wang et al. | |
| 2015/0166990 A1* | 6/2015 | Avkin-Nachum | C12N 15/113 514/44 A |
| 2016/0045526 A1* | 2/2016 | Girijavallabhan | A61K 31/7056 424/85.7 |
| 2016/0152979 A1* | 6/2016 | Avkin-Nachum | C12N 15/113 424/94.1 |

FOREIGN PATENT DOCUMENTS

| | | |
|---|---|---|
| EP | 0586520 | 3/1994 |
| EP | 0618925 | 10/1994 |
| WO | WO-93/09127 | 5/1993 |

(Continued)

OTHER PUBLICATIONS

International Search Report of International Application No. PCT/IL2013/050461 dated Oct. 11, 2013.

(Continued)

*Primary Examiner* — Lawrence E Crane
(74) *Attorney, Agent, or Firm* — Pearl Cohen Zedek Latzer Baratz LLP

(57) ABSTRACT

The present invention relates to pyrazolotriazolyl nucleoside analogs, such as

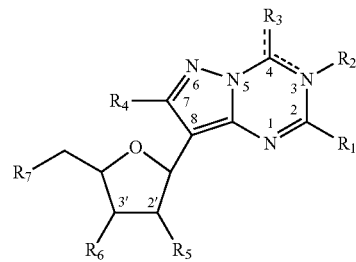

oligonucleotide comprising them, and uses in treatment of hepatitis C virus infections. Further the invention relates to a method for reducing gene expression in a cell comprising transfecting the cell with such an oligonucleotide.

6 Claims, 5 Drawing Sheets

(56) References Cited

FOREIGN PATENT DOCUMENTS

| WO | WO-93/16094 | 9/1993 |
|----|----|----|
| WO | WO 2002/032920 | 4/2002 |
| WO | WO-2003/093290 | 3/2004 |
| WO | WO-2007/002191 | 12/2007 |

OTHER PUBLICATIONS

Wellington et al. "A Review: Synthesis of aryl c-glycosides via the heck coupling reaction." Nucleosides Nucleotides Nucleic Acids, 2006 ;vol. 25 No. 12, pp. 1309-1333.

Stambasky et al, "C-Nucleosides: Syntetic Strategies and Biological Applications" Chemical Reviews, 2009, Vo. 109, No. 12, pp. 6729-6724.

Tam et al, "Nucleosides CV. Synthesis of the 8-(($\beta$-D-ribofuranosyl)pyrazolo[1,5-a]-1,3,5-triazine isosteres of adenosine and inosine", J. Heterocyclic Chemistry, Dec. 1976, pp. 1305-1308.

Tam et al. "Nucleosides. 112. Synthesis of Some New Pyrazolo[1,5-a]-1,3,5-triazines and Their C-Nucleosides[1,2]" J. Org. Chem., 1979, vol. 44, No. 25, pp. 4547-4553.

Miller et al., "Adenosine Kinase from Rabbit Liver", The Journal of Biological Chemistry, vol. 254, No. 7, Apr. 10, 1979, pp. 2346-2352.

Otter et al. "Conformational Properties of Purine-like C-nucleosides" Nucleosides & Nucleotides, 1996 vol. 15 No. 1-3m pp. 793-807.

Liang et al "Synthesis of L-ribofuransyl C-nucleosides" Carbohydrate Research vol. 303, 1997, pp. 33-38.

Zarubin et al. "Theoretical study of antagonists and inhibitors of mammalian adenosine deaminase. II. Isomeric aza-deazaanalogues of adenosine", Russian Journal of Bioorganic Chemistry, 2002, vol. 28, No. 5, pp. 404-411.

Zarubin. "Theoretical research of adenosine and its isosteric analogues. Possible mechanism of their acceptance in mammals' adenosine deaminase active center." Samara State University bulletin, Natural Science 2003, vol. 2, pp. 152-173.

Il'icheva et al. "Theoretical study of the structure of adenosine deaminase complexes with adenosine analogues: I. Aza-, deaza- and isomeric azadeazaanalogues of adenosine", Russian Journal of Bioorganic Chemistry, 2005, vol. 31, No. 5, pp. 439-452.

Raboisson et al. "A general approach toward the synthesis of C-nucleoside pyrazolo[1,5-a]-1,3,5-triazines and their 3',5'-bisphosphate C-nucleotide analogues as the first reported in vivo stable P2Y(1)-receptor antagonists." J. Org Chem.m Nov. 15, 2002. vol. 67, No. 23, pp. 8063-8071.

Raboisson et al, "Cyclic nucleotide phosphodiesterase type 4 inhibitors: Evaluation of pyrazolo [1,5-a)-1,3,5-triazine ring system as an adenine bioisostere" European Journal of Medicinal Chemistry, vol. 43, 2008, pp. 816-829.

Mathieu et al. "Stereoselective synthesis of 3'-substituted 2'-deoxy C-nucleoside pyrazolo[1,5-a]-1,3,5-triazines and their 5'-phosphate nucleotides." Tetrahedron Letters, 2006, vol. 47. pp. 5099-5103.

Arai et al. "Regiospesific Reaction of Enol Ethers with an Organopalladium Salt. Stereochemical and Conformational Effects on Product Formation" Journal of the American Chemical Society, Jan. 4, 1978, vol. 100, No. 1. pp. 287-288.

Daves, "C-Glycoside Synthesis by Palladium-Mediated Glycal-Aglycon Coupling Reaction" Acc. Chem. Res. 1990, vol. 23 No. 6, pp. 201-206.

Zhang et al. "Palladium-mediated coupling reactions of an amino-substituted heterocycle. Direct synthesis of C-nucleosides related to adenosine" Nucleosides & Nucleotides, vol. 14, No. 1-2, pp. 105-116, 1995.

Dellinger et al. "Synthesis of DNA Using a New Two-Step Cycle" Methods in Molecular Biology, Feb. 2005, vol. 288. pp. 1-16.

Sproat. RNA Synthesis Using 2'-O-(Tert-Butyldimethylsilyl) Protection, Methods in Molecular Biology, Feb. 2005, vol. 288. pp. 17-32.

Hartsel et al. "RNA Oligonucleotide Synthesis Via 5'Silyl-2'-Orthoester Chemistry", Methods in Molecular Biology, Feb. 2005, vol. 288. pp. 33-50.

Stawinski et al. "Di- and Oligonucleotide Synthesis Using H-Phosphonate Chemistry", Methods in Molecular Biology, Feb. 2005, vol. 288. pp. 81-100.

Pedroso et al. "Solid-PhaseSynthesis of Circular Oligonucleotides" Methods in Molecular Biology, Feb. 2005, vol. 288. pp. 101-126.

Chu et al. "Nucleosides. 117. Synthesis of 4-oxo-8-($\beta$-D-ribofuranosyl)-3H-pyrazolo[1,5-a]-1,3,5-triazine (OPTR) via 3-amino-2N-carbamoyl-4-($\beta$-D-ribofuranosyl)pyrazole (ACPR) derivatives" Journal of Heterocyclic Chemistry Nov. 1980, pp. 1435-1439. vol. 17, No. 7.

Schaller et al. "Studies on Polynucleotides. XXIV.1 The Stepwise Synthesis of Specific Deoxyribopolynucleotides (4).2 Protected Derivatives of Deoxyribonucleosides and New Syntheses of Deoxyribonucleoside-3" J. Am. Chem. Soc., Dec. 1963, vol. 82, No. 23, pp. 3821-3827.

Hayakawa et al. "The Allylic Protection Method in Solid-Phase Oligonucleotide Synthesis. An Efficient Preparation of Solid-Anchored DNA Oligomers" J. Am. Chem. Soc. 1990, vol. 122, No. 5, pp. 1691-1696.

Cheng at al. "Facile synthesis of 2'-deoxy-3'-keto- and 2'-deoxypseudouridine derivatives and analogues. Palladium(II)-mediated coupling reactions of furanoid glycals", J. Am. Chem. Soc., Aug. 1986, vol. 51, No. 16, pp. 3093-3098.

Larsen et al. "A new and Easy Synthesis of Silylated Furnoid Glycals in One Step from Nucleosides" Synthesis, Oct. 1994, pp. 1037-1038.

Extended European search report for EP patent application No. 13798069.4 dated Jan. 4, 2016.

* cited by examiner

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: oligonucleotides
<220> FEATURE:
<221> NAME/KEY: misc_feature
<222> LOCATION: (12)..(12)
<223> OTHER INFORMATION: n=adenosine analogue

<400> SEQUENCE: 1
taccgcgtgc anccctct                                                 18

<210> SEQ ID NO 2
<211> LENGTH: 18
<212> TYPE: DNA
<213> ORGANISM: Artificial Sequence
<220> FEATURE:
<223> OTHER INFORMATION: oligonucleotides
<220> FEATURE:
<221> NAME/KEY: misc_feature
<222> LOCATION: (2)..(2)
<223> OTHER INFORMATION: n=adenosine analogue
<220> FEATURE:
<221> NAME/KEY: misc_feature
<222> LOCATION: (12)..(12)
<223> OTHER INFORMATION: n=adenosine analogue

<400> SEQUENCE: 2
tnccgcgtgc anccctct                                                 18

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (12)..(12)
```

```
<223> OTHER INFORMATION: n=adenosine analogue

<400> SEQUENCE: 3
ttcctctttc tnccctct                                                  18

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (10)..(10)
<223> OTHER INFORMATION: n= A, C, G or T

<400> SEQUENCE: 4
acaagagggn tgcacgcggt agga                                           24

<210> SEQ ID NO 5
<211> LENGTH: 18
<212> TYPE: DNA
<213> ORGANISM: Artificial Sequence
<220> FEATURE:
<223> OTHER INFORMATION: Oligonucleotides

<400> SEQUENCE: 5
taccgcgtgc aaccctct                                                  18

<210> SEQ ID NO 6
<211> LENGTH: 18
<212> TYPE: DNA
<213> ORGANISM: Artificial Sequence
<220> FEATURE:
<223> OTHER INFORMATION: Oligonucleotides

<400> SEQUENCE: 6
ttcctctttc taccctct                                                  18
```

PYRAZOLOTRIAZOLYL NUCLEOSIDE ANALOGUES AND OLIGONUCLEOTIDES COMPRISING THEM

CROSS-REFERENCE TO RELATED APPLICATIONS

This application is a National Phase Application of PCT International Application No. PCT/IL2013/050461, International Filing Date May 30, 2013, claiming the benefit of U.S. Provisional Patent Application No. 61/653,528, filed May 31, 2012, which are both hereby incorporated by reference.

TECHNICAL FIELD

The present invention relates to pyrazolotriazolyl nucleoside analogues, oligonucleotide comprising them, and uses thereof.

BACKGROUND ART

Nucleoside analogues became increasingly important in various genetic studies and in genetic engineering. These compounds can be inserted into oligonucleotide sequences thereby proving the structure and functions of different parts of such nucleic acids, and have also the potential of being used as complex vectors that may eventually include target-drugs. The target-nucleosides thus engineered bind the nucleic acid sequence containing a mutated sequence associated with a particular disease or disorder, and the drug efficiency is thus dramatically increased while side effects are similarly reduced.

Various classes of nucleoside analogues have been reported, and among those having similar structures and H-bonding capabilities, the C-nucleosides attracted attention due to the increased stability of the glycoside bond towards enzymes and in acidic conditions.

A broad range of C-nucleosides with bicyclic, heterocyclic purine-mimics moieties have been recently reviewed (Wellington and Benner, 2006; Stambasky et al., 2009). Particular such C-nucleosides are pyrazolo[1,5a]-1,3,5-triazine derivatives, which are structurally related to purines and have similar biophysical and chemical properties.

A particular C-nucleoside discussed in the scientific literature is 4-amino-8-(β-D-ribofuranosyl)pyrazolo[1,5-a]-1,3,5-triazine. Tam et al. (1976) show the syntheses of 4-amino-8-(β-D-ribofuranosyl)pyrazolo[1,5-a]-1,3,5-triazine and 4-oxo-3H-8-(β-D-ribofuranosyl)pyrazolo-[1,5-a]-1,3,5-triazine, identified therein as compounds 10 and 16, respectively, and disclose that compound 10 has a moderate inhibitory activity against various mouse leukemia cells, and it is more active than formycin in all systems tested. Tam et al. (1979) describe the synthesis of certain C-7 ribosylated pyrazolo[1,5-a]-1,3,5-triazine C-nucleosides starting from the aforesaid 4-amino-8-(β-D-ribofuranosyl)pyrazolo[1,5-a]-1,3,5-triazine; however, do not show any biological activity of the compounds prepared. Miller et al. (1979) disclose kinetic constants for substrates and inhibitors of highly purified rabbit liver adenosine kinase for dozens of nucleosides and nucleoside analogues including 4-amino-8-(β-D-ribofuranosyl)pyrazolo[1,5-a]-1,3,5-triazine, identified therein as compound 94. Otter and Klein (1996) describe NMR study of various purine-like C-nucleosides including the pyrazolotriazolyl nucleoside analogues 4-amino-8-(β-D-ribofuranosyl) pyrazolo[1,5-a]-1,3,5-triazine and 4-methyl-thio-8-(β-D-ribofuranosyl)pyrazolo[1,5-a]-1,3,5-triazine, identified therein as compounds 4 and 5, respectively; however, do not show any biological activity of the compounds prepared. Liang et al (1997) describe a process for the synthesis of, inter alia, 4-amino-8-(β-L-ribofuranosyl)pyrazolo[1,5-a]-1,3,5-triazine, and disclose that no significant anti-HBV and anti-HIV activities were observed for this compound. WO 2002032920 discloses compositions and methods for treatment of a Flaviviridae, Orthomyxoviridae or Paramyxoviridae infection, or conditions related to abnormal cellular proliferation, using certain nucleoside analogues including pyrazol-triazine based nucleosides, in particular, 4-amino-8-(β-D-ribofuranosyl)pyrazolo[1,5-a]-1,3,5-triazine. Zarubin et al. (2002) disclose a theoretical study of antagonists and inhibitors of mammalian adenosine deaminase (ADA), in particular, certain isomeric aza-deaza analogues of adenosine and their N1-protonated forms, including the compound 4-amino-8-(β-D-ribofuranosyl)pyrazolo[1,5-a]-1,3,5-triazine, identified therein as $z^5c^9$Ado, and its 1-N protonated form, identified therein as $1H^+$-$z^5c^9$Ado. Zarubin et al. (2003) describe computer modeling studies to find relationships between the molecular structure of certain isosteric analogues of adenosine, including their N1-protonated forms (except for that of 1-deaza analogues), and substrate properties for the mammalian ADA. This reference refers, inter alia, to D-ribitol, 1-C-(4-aminopyrazolo[1,5-a]-1,3,5-triazin-8-yl)-1,4-anhydro-,(1S), which is a chiral isomer of the aforementioned 4-amino-8-Q3-D-ribofuranosyl) pyrazolo[1,5-a]-1,3,5-triazine. Il'icheva et al. (2005) disclose conformational models of the active site of ADA and its complexes in the basic state with adenosine and various isosteric analogues of the aza, deaza, and azadeaza series, including the aforementioned $z^5c^9$Ado. WO 2007002191 discloses a method for the preparation of 9-deazapurine derivatives, including (2S,3R,4S,5R)-2-(4-aminopyrazolo[1,5-a][1,3,5]triazin-8-yl)-5-(hydroxymethyl)-tetrahydrofuran-3,4-diol and (2S,3R,4R,5R)-2-(4-aminopyrazolo[1,5-a][1,3,5]triazin-8-yl)-5-(hydroxyl methyl)-3-methyl-tetrahydrofuran-3,4-diol, identified therein as compounds 9-3 and 9-3', respectively; however, does not show any biological activity of these compounds.

WO 2003093290 discloses nucleosides derivatives in which each one of the carbon atoms at positions 2' and 3' of the ribose moiety is substituted with a hydroxyl group, but at least one of said carbon atoms is further substituted with a group different than hydrogen. Examples of such nucleosides include, inter alia, 8-(2'-C-methyl-β-D-ribofuranosyl)-pyrazolo[1,5-a][1,3,5]triazin-4-ylamine, 8-(2'-C-methyl-(3-D-ribofuranosyl)-3H-pyrazolo[1,5-a]-[1,3,5]triazin-4-one, and 2-amino-8-(2'-C-methyl-β-D-ribofuranosyl)-3H-pyrazolo-[1,5a][1,3,5]triazin-4-one, identified therein as compounds 98-100, respectively. According to this publication, these compounds are useful in treatment of hepatitis C virus infections.

The syntheses of several deoxyadenosine C-nucleoside analogues having a pyrazolotriazine heterocycle as a base have also been reported. Raboisson et al. (2002) disclose large-scale preparation of 2'-deoxy-C-nucleosides of pyrazolo[1,5-a]-1,3,5-triazines, such as 8-(2'-deoxy-β-D-ribofuranosyl)-2-methyl-4-(N-methyl amino)pyrazolo[1,5-a]-1,3,5-triazine-3',5'-bisphosphate; 8-(2'-deoxy-β-D-ribofuranosyl)-2-methyl-4-(N-methyl-N-phenylamino)-pyrazolo[1,5-a]-1,3,5-triazine-3',5'-bisphosphate; and 8-(2'-deoxy-β-D-ribofuranosyl)-2-methyl-4-(N-methyl amino)pyrazolo[1,5-a]-1,3,5-triazine, identified therein as compounds 2, 20 and 21, respectively; and further disclose that compound 2 strongly inhibits ADP-induced human platelet aggregation and shape change. Raboisson et al. (2008) disclose cyclic nucleotide phosphodiesterase type 4 inhibitors, in particular, pyrazolo[1,5-a]-1,3,5-triazine ring systems as adenine bioisosteres, including pyrazolo[1,5-a]-1,3,5-triazine compounds substituted at position 8, and that some of those compounds strongly inhibit lipopolysaccharide (LPS)-induced TNFα release from human mononuclear cells from healthy subjects. Mathieu et al. (2006) show stereoselective synthesis of 3'-substituted 2'-deoxy C-nucleoside pyrazolo[1,5-a]-1,3,5-triazines and their 5'-phosphate nucleotides including 8-(2'-deoxy-β-D-ribofuranosyl)-2-methyl-4-(N-methylamino)pyrazolo[1,5-a]-1,3,5-triazine-3',5'-bisphosphate, identified therein as compound 1, and certain analogues thereof.

WO 9316094 discloses structural analogues of the six N-nucleosides commonly found in RNA and DNA, which are said to be inherently fluorescent under physiological conditions, including pyrazolo-triazine based nucleoside analogues; however, exemplifies formycin-A based derivatives only, i.e., pyrazolo-pyrimidine nucleoside analogues. As stated in this publication, such analogues may be incorporated into DNA and/or RNA oligonucleotides to produce fluorescent oligonucleotides having prescribed sequences, which may be used for detection assays.

C-nucleosides can be synthesized using different strategies such as building up of an aglycon on a carbohydrate residue or vice versa; modifying existing C-nucleosides; and direct coupling of a suitable preformed heterocyclic aglycon with the carbohydrate unit (Stambasky et al., 2009). The latter is of great interest since it consists of a direct C—C attachment of the preformed base analogue to the deoxyribose unit in a highly stereo and regioselective manner using the Heck cross-coupling reaction initially reported by Daves (Arai and Daves, 1978; Daves, 1990). Thus, when an iodopyrazolotriazine aglycon is reacted with a protected glycal using the Heck reaction, the new C-glycosidic bond is formed selectively at the anomeric carbon, despite the presence of a rich-electron double-bond. The initial attack occurs from the less hindered face of the glycal ring, and this regioselective effect may be enhanced when a bulky protective group is present in the 3-position, in combination with a bulky Pd-catalyst ligand (Zhang et al., 1995). A few examples of unexpected exclusive β-anomer formation using a fully unprotected glycal have also been described (Raboisson et al., 2002; Zhang et al., 1995).

SUMMARY OF INVENTION

It has been found, in accordance with the present invention, that certain pyrazolotriazolyl-based nucleoside analogues such as 8-[3'-(2-cyanoethyl)-(N,N-diisopropyl)]-phosphoramidite-(2'-deoxy-5'-dimethoxytrityl-β-D-ribofuranozyl)-4-(N-benzoylamino)-pyrazolo[1,5a]-1,3,5-triazine, can be incorporated into oligonucleotides, substituting natural purine nucleosides and imparting acid stability and nuclease stability to the oligonucleotide. Furthermore, oligonucleotides comprising one or more such nucleoside analogues are capable of hybridizing with oligonucleotides having complementary sequences thereto in which no such analogues are incorporated.

In one aspect, the present invention thus relates to a nucleoside analogue of the general formula I:

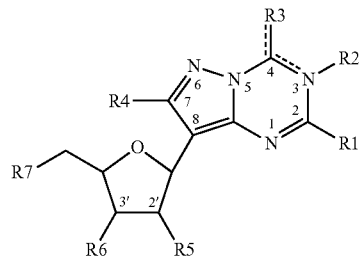

wherein
$R_1$ and $R_4$ each independently is selected from H, halogen, —CN, —SCN, —NO$_2$, —O-hydrocarbyl, —S-hydrocarbyl, —CO—H, —CO-hydrocarbyl, —NR$_8$R$_9$, heteroaryl, or hydrocarbyl optionally substituted by one or more groups each independently is halogen, —CN, —SCN, or —NO$_2$, wherein $R_8$ and $R_9$ are each independently H, hydrocarbyl or an amine protecting group; or $R_8$ and $R_9$ together with the nitrogen atom to which they are attached form a saturated or unsaturated heterocyclic ring optionally containing 1-2 further heteroatoms selected from oxygen, nitrogen or sulfur;
$R_2$ is H or absent;
$R_3$ is O or —NR$_{10}$R$_{10'}$, wherein $R_{10}$ and $R_{10'}$ are each independently H, hydrocarbyl, —CO-hydrocarbyl, or an amine protecting group;
$R_5$ is H, halogen, —O$^-$, or —OR$_{11}$;
$R_6$ is —O$^-$, or —OR$_{11}$;
$R_7$ is —OR$_{11}$, or a phosphate moiety;
$R_{11}$ each independently is H, (C$_1$-C$_8$)alkyl, (C$_1$-C$_8$)alkylene-OR$_{12}$, (C$_1$-C$_8$)alkylene-SR$_{12}$, (C$_1$-C$_8$)alkylene-NR$_{12}$R$_{13}$, a hydroxyl protecting group, or a phosphoramidite moiety of the formula —P(OR$_{14}$)NR$_{15}$R$_{16}$, wherein $R_{14}$ is H or cyano-(C$_1$-C$_8$)alkyl, preferably cyanoethyl, and $R_{15}$ and $R_{16}$ each independently is H or (C$_1$-C$_8$)alkyl, preferably isopropyl;
$R_{12}$ and $R_{13}$ each independently is H or (C$_1$-C$_8$)alkyl; and
the dotted line represents a potential double bond between the carbon atom at position 4 and either the nitrogen atom at position 3 or the radical $R_3$, provided that, when $R_2$ is H, there is a double bond between the carbon atom at position 4 and $R_3$, and when $R_2$ is absent, there is a double bond between the carbon atom at position 4 and the nitrogen atom at position 3,
but excluding the analogues wherein $R_5$ and $R_6$ each independently is —OH or —O$^-$, and the analogues wherein $R_5$ is H and $R_1$ is hydrocarbyl.

In another aspect, the present invention provides an oligonucleotide comprising one or more nucleoside analogues each independently of the general formula II:

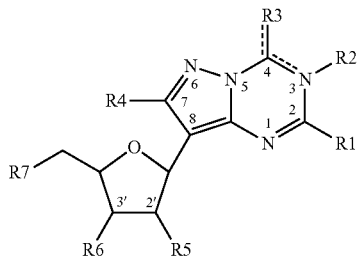

wherein $R_1$ and $R_4$ each independently is selected from H, halogen, —CN, —SCN, —NO$_2$, —O-hydrocarbyl, —S-hydrocarbyl, —CO—H, —CO-hydrocarbyl, —NR$_8$R$_9$, heteroaryl, or hydrocarbyl optionally substituted by one or more groups each independently is halogen, —CN, —SCN, or —NO$_2$, wherein $R_8$ and $R_9$ are each independently H, hydrocarbyl or an amine protecting group; or $R_8$ and $R_9$ together with the nitrogen atom to which they are attached form a saturated or unsaturated heterocyclic ring optionally containing 1-2 further heteroatoms selected from oxygen, nitrogen or sulfur;

$R_2$ is H or absent;

$R_3$ is O or —NR$_{10}$R$_{10'}$, wherein $R_{10}$ and $R_{10'}$ are each independently H, hydrocarbyl, or —CO-hydrocarbyl;

$R_5$ is H, halogen, —O$^-$, or —OR$_{11}$;

$R_6$ is —O$^-$, or —OR$_{11}$;

$R_7$ is —OR$_{11}$, a monophosphate moiety, or a phosphate linking moiety;

$R_{11}$ each independently is H, (C$_1$-C$_8$)alkyl, (C$_1$-C$_8$)alkylene-OR$_{12}$, (C$_1$-C$_8$)alkylene-SR$_{12}$, or (C$_1$-C$_8$)alkylene-NR$_{12}$R$_{13}$, wherein $R_{12}$ and $R_{13}$ each independently is H or (C$_1$-C$_8$)alkyl; and the dotted line represents a potential double bond between the carbon atom at position 4 and either the nitrogen atom at position 3 or the radical $R_3$, provided that, when $R_2$ is H, there is a double bond between the carbon atom at position 4 and $R_3$, and when $R_2$ is absent, there is a double bond between the carbon atom at position 4 and the nitrogen atom at position 3.

In one particular aspect, the oligonucleotide of the invention is a DNA oligonucleotide comprising one or more nucleoside analogues each independently of the general formula II, wherein $R_5$ is H or halogen; $R_6$ is —O$^-$, or —OR$_{11}$; and $R_{11}$ is H, (C$_1$-C$_8$)alkyl, (C$_1$-C$_8$)alkylene-OR$_{12}$, (C$_1$-C$_8$)alkylene-SR$_{12}$, or (C$_1$-C$_8$)alkylene-NR$_{12}$R$_{13}$, wherein $R_{12}$ and $R_{13}$ each independently is H or (C$_1$-C$_8$) alkyl.

In another particular aspect, the oligonucleotide of the invention is an RNA oligonucleotide comprising one or more nucleoside analogues each independently of the general formula II, wherein $R_5$ is —O$^-$, or —OR$_{11}$; $R_6$ is —O$^-$, or —OR$_{11}$; and $R_{11}$ each independently is H, (C$_1$-C$_8$)alkyl, (C$_1$-C$_8$)alkylene-OR$_{12}$, (C$_1$-C$_8$)alkylene-SR$_{12}$, or (C$_1$-C$_8$) alkylene-NR$_{12}$R$_{13}$, wherein $R_{12}$ and $R_{13}$ each independently is H or (C$_1$-C$_8$)alkyl.

In some embodiments about 5. 10, 20, 30, 40, 50, 60, 70, 80, 90 or 100% of the bases in a sequence may be replaced by PT nucleotide analogues.

In a further aspect, the present invention provides a double-stranded DNA molecule, wherein at least one strand is a DNA oligonucleotide as defined above. In particular such aspects, the invention provides a double-stranded DNA molecule, wherein either one strand is a DNA oligonucleotide as defined above, or both strands are DNA oligonucleotides each independently as defined above.

In still another aspect, the present invention provides a pharmaceutical composition comprising a nucleoside analogue of the general formula I as defined above, and a pharmaceutically acceptable carrier.

In yet another aspect, the present invention provides a pharmaceutical composition comprising a DNA oligonucleotide as defined above; or an RNA oligonucleotide as defined above; or a double-stranded DNA molecule as defined above, and a pharmaceutically acceptable carrier.

In still a further aspect, the present invention provides an expression vector comprising a double-stranded DNA molecule as defined above.

In yet a further aspect, the present invention relates to a method for reducing gene expression in a cell comprising transfecting said cell with an oligonucleotide as defined above, or with an expression vector as defined above.

DETAILED DESCRIPTION OF THE INVENTION

Figure 1:
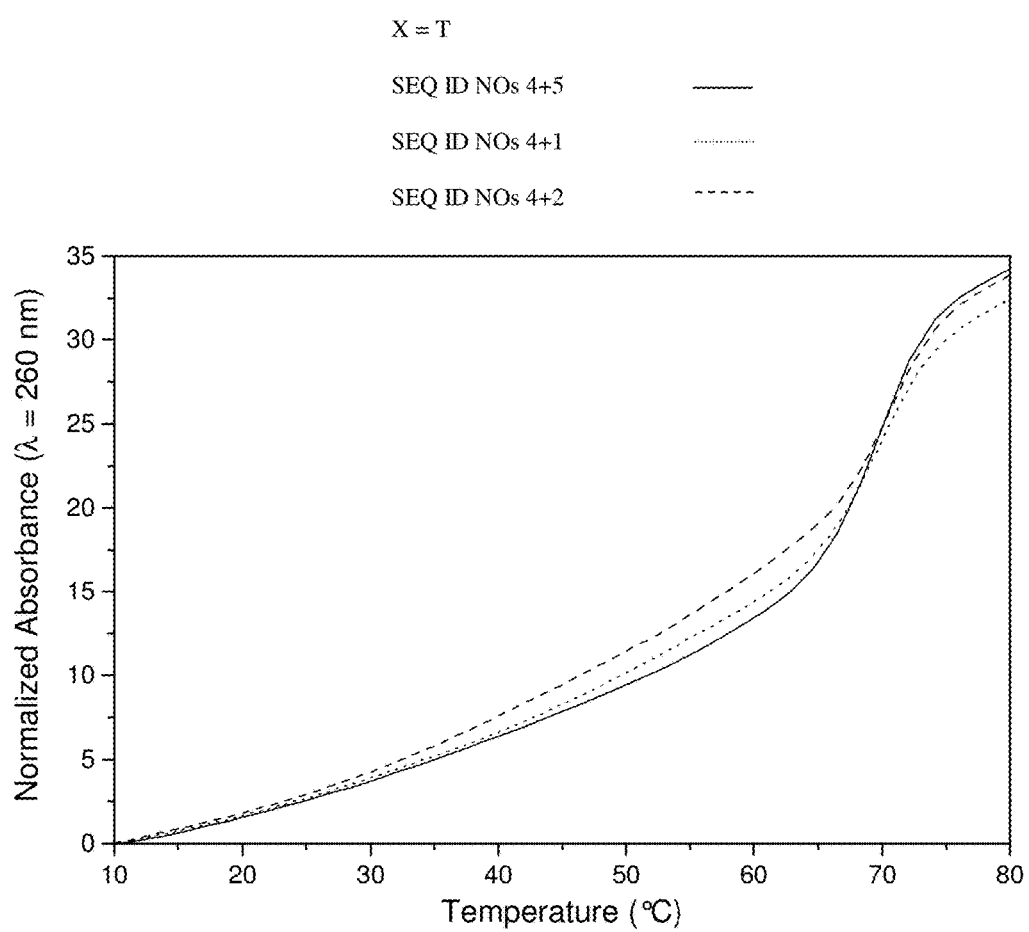
FIG. 1 shows thermal denaturation curves for the duplexes obtained by hybridization of the oligonucleotides of SEQ ID NO: 4 (X=T)+SEQ ID NO: 5, SEQ ID NO: 4 (X=T)+SEQ ID NO: 1 and SEQ ID NO: 4 (X=T)+SEQ ID NO: 2. Oligonucleotide concentrations were 1 μM (each strand) in a 10 mM sodium phosphate, pH 7, buffer containing 150 mM NaCl and 1 mM EDTA. Temperature was increased from 10° C. to 80° C. over 140 min. Melting curves were recorded at X, =260 nm.

The present invention relates, in one aspect, to pyrazolotriazolyl-based nucleoside analogues of the general formula I as defined above, but excluding the compounds wherein the radicals linked to the carbon atoms at positions 2' and 3' of the ribose moiety, i.e., $R_5$ and $R_6$, each independently is —OH or —O$^-$, and the compounds wherein the radical linked to the carbon atom at position 2' of the ribose moiety, i.e., $R_5$, is H and the radical linked to the carbon atom at position 2 of the base, i.e., $R_1$, is hydrocarbyl. The pyrazolotriazolyl-based nucleoside analogues of the invention may alternatively be defined as compounds of the general formula I as defined above, provided that at least one of the radicals linked to the carbon atoms at positions 2' and 3' of the ribose moiety, i.e., $R_5$ and $R_6$, is —OR$_{11}$, wherein $R_{11}$ is not H.

As used herein, the term "halogen" includes fluoro, chloro, bromo, and iodo, and is preferably fluoro or chloro.

The term "hydrocarbyl" in any of the definitions of the different radicals $R_1$, $R_3$ and $R_4$ refers to a radical containing only carbon and hydrogen atoms that may be saturated or unsaturated, linear or branched, cyclic or acyclic, or aromatic, and includes (C$_1$-C$_8$)alkyl, (C$_2$-C$_8$)alkenyl, (C$_2$-C$_8$) alkynyl, (C$_3$-C$_{10}$)cycloalkyl, (C$_3$-C$_{10}$)cycloalkenyl, (C$_6$-C$_{14}$)aryl, (C$_1$-C$_8$)alkyl(C$_6$-C$_{14}$)aryl, and (C$_6$-C$_{14}$)aryl(C$_1$-C$_8$)alkyl.

The term "($C_1$-$C_8$)alkyl" typically means a straight or branched hydrocarbon radical having 1-8 carbon atoms and includes, e.g., methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like. Preferred are ($C_1$-$C_4$)alkyl groups, most preferably methyl and ethyl. The terms "($C_2$-$C_8$)alkenyl" and "($C_2$-$C_8$)alkynyl" typically mean straight and branched hydrocarbon radicals having 2-8 carbon atoms and 1 double or triple bond, respectively, and include ethenyl, 3-buten-1-yl, 2-ethenylbutyl, 3-octen-1-yl, and the like, and propynyl, 2-butyn-1-yl, 3-pentyn-1-yl, and the like. ($C_2$-$C_6$)alkenyl and ($C_2$-$C_6$)alkynyl radicals are preferred, more preferably ($C_2$-$C_4$)alkenyl and ($C_2$-$C_4$)alkynyl.

The term "($C_1$-$C_8$)alkylene" typically means a divalent straight or branched hydrocarbon radical having 1-8 carbon atoms and includes, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, and the like. Preferred are ($C_1$-$C_4$)alkylene, more preferably ($C_1$-$C_2$)alkylene.

The term "($C_3$-$C_{10}$)cycloalkyl" as used herein means a mono- or bicyclic saturated hydrocarbyl group having 3-10 carbon atoms such as cyclopropyl, cyclobutyl, cyclopentyl, cyclohexyl, cycloheptyl, cyclooctyl, adamantyl, bicyclo[3.2.1]octyl, bicyclo[2.2.1]heptyl, and the like, that may be substituted, e.g., by one or more $C_1$-$C_8$ alkyl groups.

The term "($C_3$-$C_{10}$)cycloalkenyl" as used herein means a mono- or bicyclic hydrocarbyl group having 3-10 carbon atoms and 1 double bond such as cyclopropenyl, cyclobutenyl, cyclopentenyl, cyclohexenyl, cycloheptenyl, cyclooctenyl, 1,2,3,3a,4,5-hexahydropentalenyl, 1,2,3,3a,4,6a-hexahydropentalenyl, 2,3,3a,4,5,6-hexahydro-1H-indenyl, 2,3,3a,4,5,7a-hexahydro-1H-indenyl, 2,3,3a,4,7,7a-hexahydro-1H-indenyl, 3a,4,5,6,7,7a-hexahydro-1H-indenyl, 1,2,3,4,4a,5,6,8a-octahydronaphthalenyl, 1,2,3,4,4a,5,8,8a-octahydronaphthalenyl, and the like, that may be substituted, e.g., by one or more $C_1$-$C_8$ alkyl groups.

The term "($C_6$-$C_{14}$)aryl" denotes an aromatic carbocyclic group having 6-14 carbon atoms consisting of a single ring or multiple rings either condensed or linked by a covalent bond such as, but not limited to, phenyl, naphthyl, phenanthryl, and biphenyl. The aryl radical may optionally be substituted by one or more groups each independently selected from halogen, e.g., F, Cl, Br or I, ($C_1$-$C_8$)alkyl, —O—($C_1$-$C_8$)alkyl, —COO($C_1$-$C_8$)alkyl, —CN, or $NO_2$.

The term "($C_6$-$C_{14}$)aryl($C_1$-$C_8$)alkyl" denotes an arylalkyl radical such as benzyl, phenetyl, and the like, and the term "($C_1$-$C_8$)alkyl($C_6$-$C_{14}$)aryl" denotes an alkylaryl radical such as methylphenyl, ethylphenyl, xylyl, and the like.

The term "heteroaryl" refers to a radical derived from a mono- or polycyclic heteroaromatic ring containing one to three, preferably 1-2, heteroatoms selected from N, O or S. When the heteroaryl is a monocyclic ring, it is preferably a radical of a 5-6-membered ring such as, but not limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-triazinyl, 1,3,4-triazinyl, and 1,3,5-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-a]pyridyl, benzimidazolyl, benzthiazolyl, benzoxazolyl, pyrido[1,2-a]pyrimidinyl and 1,3-benzodioxinyl. The heteroaryl may be substituted. It is to be understood that when a polycyclic heteroaryl is substituted, the substitution may be in any of the carbocyclic and/or heterocyclic rings.

In certain embodiments, the nucleoside analogue of the present invention is a compound of the general formula I as defined above, wherein $R_1$ and $R_4$ each independently is H, halogen, —CN, —SCN, —$NO_2$, —O-hydrocarbyl, —S-hydrocarbyl, —CO—H, —CO-hydrocarbyl, —$NR_8R_9$, heteroaryl, or hydrocarbyl; $R_8$ and $R_9$ are each independently H, hydrocarbyl, or an amine protecting group; and said hydrocarbyl each independently is ($C_1$-$C_8$)alkyl, preferably ($C_1$-$C_4$)alkyl, more preferably methyl or ethyl. In particular such embodiments, $R_1$ and $R_4$ each independently is H, halogen, —O-hydrocarbyl, —S-hydrocarbyl, —CO—H, —CO-hydrocarbyl, —$NR_8R_9$, or hydrocarbyl; $R_8$ and $R_9$ are each independently H, hydrocarbyl, or an amine protecting group; and said hydrocarbyl each independently is ($C_1$-$C_4$)alkyl, preferably methyl or ethyl.

In certain embodiments, the nucleoside analogue of the present invention is a compound of the general formula I as defined above, wherein $R_3$ is O or —$NR_{10}R_{10'}$, wherein $R_{10}$ and $R_{10'}$ are each independently H, hydrocarbyl, —CO—hydrocarbyl, or an amine protecting group; and said hydrocarbyl is ($C_1$-$C_8$)alkyl, preferably ($C_1$-$C_4$)alkyl, most preferably methyl or ethyl.

In certain embodiments, the nucleoside analogue of the present invention is a compound of the general formula I as defined above, wherein $R_5$ is H, halogen, —$O^-$, or —$OR_{11}$; $R_{11}$ is H, ($C_1$-$C_4$)alkyl, preferably ($C_1$-$C_2$)alkyl, ($C_1$-$C_4$)alkylene-$OR_{12}$, preferably ($C_1$-$C_2$)alkylene-$OR_{12}$, ($C_1$-$C_4$)alkylene-$SR_{12}$, preferably ($C_1$-$C_2$)alkylene-$SR_{12}$, ($C_1$-$C_4$)alkylene-$NR_{12}R_{13}$, preferably ($C_1$-$C_2$)alkylene-$NR_{12}R_{13}$, a hydroxyl protecting group, or a phosphoramidite moiety of the formula —P($OR_{14}$)$NR_{15}R_{16}$; $R_{12}$ and $R_{13}$ each independently is H or ($C_1$-$C_4$)alkyl, preferably ($C_1$-$C_2$)alkyl; $R_{14}$ is H or cyano-($C_1$-$C_8$)alkyl, preferably cyanoethyl; and $R_{15}$ and $R_{16}$ each independently is H or ($C_1$-$C_8$)alkyl, preferably isopropyl. In particular such embodiments, $R_5$ is H, halogen, —$O^-$, or —$OR_{11}$; and $R_{11}$ is H, ($C_1$-$C_2$)alkyl, ($C_1$-$C_2$)alkylene-OH, ($C_1$-$C_2$)alkylene-$OCH_3$, ($C_1$-$C_2$)alkylene-SH, ($C_1$-$C_2$)alkylene-$SCH_3$, ($C_1$-$C_2$) alkylene-$NH_2$, a hydroxyl protecting group, or a phosphoramidite moiety of the formula —P($OR_{14}$)$NR_{15}R_{16}$, wherein $R_{14}$ is cyanoethyl, and $R_{15}$ and $R_{16}$ are isopropyl (—P(O-cyanoethyl)N(i-propyl)$_2$), i.e., a moiety of 3-((diisopropylamino)phosphineoxy) propanenitrile.

In certain embodiments, the nucleoside analogue of the present invention is a compound of the general formula I as defined above, wherein $R_6$ is —$O^-$, or —$OR_{11}$; $R_{11}$ is H, ($C_1$-$C_4$)alkyl, preferably ($C_1$-$C_2$)alkyl, ($C_1$-$C_4$)alkylene-$OR_{12}$, preferably ($C_1$-$C_2$)alkylene-$OR_{12}$, ($C_1$-$C_4$)alkylene-$SR_{12}$, preferably ($C_1$-$C_2$)alkylene-$SR_{12}$, ($C_1$-$C_4$)alkylene-$NR_{12}R_{13}$, preferably ($C_1$-$C_2$)alkylene-$NR_{12}R_{13}$, a hydroxyl protecting group, or a phosphoramidite moiety of the formula —P($OR_{14}$)$NR_{15}R_{16}$; $R_{12}$ and $R_{13}$ each independently is H or ($C_1$-$C_4$)alkyl, preferably ($C_1$-$C_2$)alkyl; $R_{14}$ is H or cyano-($C_1$-$C_8$)alkyl, preferably cyanoethyl; and $R_{15}$ and $R_{16}$ each independently is H or ($C_1$-$C_8$)alkyl, preferably isopropyl. In particular such embodiments, $R_6$ is —$O^-$, or —$OR_{11}$; and $R_{11}$ is H, ($C_1$-$C_2$)alkyl, ($C_1$-$C_2$)alkylene-OH, ($C_1$-$C_2$)alkylene-$OCH_3$, ($C_1$-$C_2$)alkylene-SH, ($C_1$-$C_2$)alkylene-$SCH_3$, ($C_1$-$C_2$)alkylene-$NH_2$, or a phosphoramidite moiety of the formula —P($OR_{14}$)$NR_{15}R_{16}$, wherein $R_{14}$ is cyanoethyl, and $R_{15}$ and $R_{16}$ are isopropyl (—P(O-cyanoethyl)N(i-propyl)$_2$).

In particular embodiments, the nucleoside analogue of the present invention is a compound of the general formula I as defined above, wherein $R_1$ and $R_4$ each independently is H, halogen, ($C_1$-$C_4$)alkyl, —O—($C_1$-$C_4$)alkyl, —S—($C_1$-$C_4$)alkyl, —CO—H, —CO—($C_1$-$C_4$)alkyl, or —$NR_8R_9$, wherein $R_8$ and $R_9$ are each independently H, $(C_1\text{-}C_4)$alkyl, or an amine protecting group; $R_3$ is O or $-NR_{10}R_{10'}$, wherein $R_{10}$ and $R_{10'}$ are each independently H, $(C_1\text{-}C_4)$ alkyl, $-CO-(C_1\text{-}C_4)$alkyl, or an amine protecting group; $R_5$ is H, halogen, $-O^-$, or $-OR_{11}$; $R_6$ is $-O^-$, or $-OR_{11}$; and $R_{11}$ each independently is H, $(C_1\text{-}C_2)$alkyl, $(C_1\text{-}C_2)$alkylene-OH, $(C_1\text{-}C_2)$alkylene-OCH$_3$, $(C_1\text{-}C_2)$alkylene-SH, $(C_1\text{-}C_2)$alkylene-SCH$_3$, $(C_1\text{-}C_2)$alkylene-NH$_2$, a hydroxyl protecting group, or $-P(O\text{-cyanoethyl})N(i\text{-propyl})_2$. In more particular embodiments, $R_1$ and $R_4$ each independently is H, halogen, $(C_1\text{-}C_2)$alkyl, $-O-(C_1\text{-}C_2)$alkyl, $-S-(C_1\text{-}C_2)$alkyl, $-CO-H$, $-CO-(C_1\text{-}C_2)$alkyl, or $-NR_8R_9$, wherein $R_8$ and $R_9$ are each independently H, $(C_1\text{-}C_2)$alkyl, or an amine protecting group; and $R_3$ is O or $-NR_{10}R_{10'}$, wherein $R_{10}$ and $R_{10'}$ are each independently H, $(C_1\text{-}C_2)$ alkyl, $-CO-(C_1\text{-}C_2)$alkyl, or an amine protecting group.

As stated above, the pyrazolotriazolyl-based nucleoside analogues of the general formula I can be used in oligonucleotide synthesis, substituting natural purine nucleosides. A deoxyribonucleoside analogue "A" of the general formula I, i.e., such a nucleoside analogue wherein the radical linked to the carbon atom at position 2' of the ribose moiety ($R_5$) is H or halogen, can be attached to another nucleoside "B", e.g., a natural or modified nucleoside or deoxynucleoside, or another nucleoside analogue of the general formula I, via a phosphodiester bond linking position 3' of deoxyribonucleoside analogue "A" and position 5' of nucleoside "B". On the other hand, a ribonucleoside analogue "A" of the general formula I, i.e., such a nucleoside analogue wherein the radicals linked to the carbon atoms at position 2' and 3' of the ribose moiety ($R_5$ and $R_6$) each independently is $-O^-$ or $-OR_{11}$, can be attached to another nucleoside "B", e.g., a natural or modified nucleoside or deoxynucleoside, or another nucleoside analogue of the general formula I, via a phosphodiester bond linking either position 2' or position 3' of ribonucleoside analogue "A" and position 5' of nucleoside "B".

Both ribonucleoside and deoxyribonucleoside analogues of the general formula I capable of forming a phosphodiester bond linking position 3' to position 5' of another nucleoside are those in which the radical linked to the carbon atom at position 3' of the ribose moiety, i.e., $R_6$, is $-OR_{11}$, wherein $R_{11}$ is a phosphoramidite moiety as defined above. Similarly, ribonucleoside analogues of the general formula I capable of forming a phosphodiester bond linking position 2' to position 5' of another nucleoside are those in which the radical linked to the carbon atom at position 2' of the ribose moiety, i.e., $R_5$, is $-OR_{11}$, wherein $R_{11}$ is a phosphoramidite moiety as defined above.

In certain embodiments, the nucleoside analogue of the present invention is a ribonucleoside analogue of the general formula I as defined above, wherein $R_5$ is $-O^-$, or $-OR_{11}$, wherein $R_{11}$ is H, $(C_1\text{-}C_8)$alkyl, $(C_1\text{-}C_8)$alkylene-OR$_{12}$, $(C_1\text{-}C_8)$alkylene-SR$_{12}$, $(C_1\text{-}C_8)$alkylene-NR$_{12}$R$_{13}$, or a hydroxyl protecting group; and $R_6$ is $-OR_{11}$, wherein $R_{11}$ is a phosphoramidite moiety of the formula $-P(OR_{14})NR_{15}R_{16}$. In other embodiments, the nucleoside analogue of the present invention is a ribonucleoside analogue of the general formula I as defined above, wherein $R_5$ is $-OR_{11}$, wherein $R_{11}$ is a phosphoramidite moiety of the formula $-P(OR_{14})NR_{15}R_{16}$; and $R_6$ is $-O^-$ or $-OR_{11}$, wherein $R_{11}$ is H, $(C_1\text{-}C_8)$alkyl, $(C_1\text{-}C_8)$alkylene-OR$_{12}$, $(C_1\text{-}C_8)$alkylene-SR$_{12}$, $(C_1\text{-}C_8)$alkylene-NR$_{12}$R$_{13}$, or a hydroxyl protecting group.

The term "amine protecting group" as used herein refers to a chemical moiety that can readily be attached to an amine group (and forming a protected amine) when desired to protect said amine from undesired chemical reactions and then at a later point be removed from said protected amine to reveal the original amine. Examples of amine protecting groups can be found in references such as Green and Wuts (1991, Protective Groups in Organic Synthesis, Wiley, New York, 2$^{nd}$ Edition) and Bodansky (1993, Principles of Peptide Synthesis, Springer, Berlin). Examples of amine protecting groups include, without being limited to, acetyl, benzoyl, carbobenzyloxy, p-methoxybenzyl carbonyl, methoxycarbonyl, tert-butyloxycarbonyl, 9-fluorenylmethyloxycarbonyl (FMOC), benzyl, a carbamate group, p-methoxybenzyl, 3,4-dimethoxybenzyl (DMPM), p-methoxyphenyl (PMP), monomethoxytrityl (MMT), dimethoxytrityl (DMT), and tosyl.

The term "hydroxyl protecting group", also termed "alcohol protecting group", refers to a chemical moiety that can readily be attached to an hydroxyl group (and forming a protected hydroxy) when desired to protect said hydroxyl from undesired chemical reactions and then at a later point be removed from said protected hydroxyl to reveal the original hydroxyl group. Examples of hydroxy protecting groups are well known in the art and can be found in references such as Green and Wuts (1991, Protective Groups in Organic Synthesis, Wiley, New York, 2$^{nd}$ Edition) and Bodansky (1993, Principles of Peptide Synthesis, Springer, Berlin). Non-limiting examples of hydroxyl protecting groups include DMT, tert-butyldimethylsilyl (TBDMS), tri-iso-propylsilyloxymethyl (TOM), trimethylsilyl (TMS), tri-isopropylsilyl (TIPS), acetyl, benzyl, and benzoyl.

The term "phosphate moiety" as used herein refers to a monophosphate moiety of the general formula $-[O-P(O)(R')-O]^{2-}$, a diphosphate moiety of the general formula $-[O-P(O)(R')-O-P(O)(R')-O]^{3-}$, or a triphosphate moiety of the general formula $-[O-P(O)(R')-O-P(O)(R')-O-P(O)(R')-O]^{4-}$, wherein R' each independently is $O^-$, $S^-$, $BH_3^-$, or $N^-$, preferably to such mono-, di- and tri-phosphate moieties wherein (i) R' each is $O^-$; or (ii) one of the R's, preferably the R' linked to the phosphate atom at position α, is $S^-$ or $BH_3^-$, and the other R's are $O^-$, as well as to any protonated form thereof. Preferred are monophosphate moieties as defined above, such as $-[O-PO_3]^{2-}$, $-[O-PO_2S]^{2-}$, and $-[O-PO_2(BH_3)]^{2-}$, more preferably $-[O-PO_3]^{2-}$.

The term "phosphate linking moiety" as used herein refers to a moiety of the general formula $-[O-P(O)(R')]^-$, wherein R' is $O^-$, $S^-$, $BH_3^-$, or $N^-$, preferably $O^-$, $S^-$, or $BH_3^-$, more preferably $O^-$, as well as to a protonated form thereof.

In certain particular embodiments, the nucleoside analogue of the present invention is a compound of the general formula I, wherein $R_2$ is absent; $R_3$ is $-NR_{10}R_{10'}$; $R_1$, $R_4$, $R_5$, $R_6$, $R_7$ $R_{10}$ and $R_{10'}$ are as defined in any one of the embodiments described above; and the dotted line represents a double bond between the carbon atom at position 4 and the nitrogen atom at position 3, i.e., an adenine PT nucleotide analogue of the general formula Ia. In other particular embodiments, the nucleoside analogue of the invention is a compound of the general formula I, wherein $R_1$ is $-NR_8R_9$; $R_2$ is H; $R_3$ is O; $R_4$ to $R_9$ are as defined in any one of the embodiments described above; and the dotted line represents a double bond between the carbon atom at position 4 and $R_3$, i.e., a guanine PT nucleotide analogue of the general formula Ib (see Table 1).

"Adenine PT nucleotide analogue" refers to a nucleotide in which the adenine base has been replaced with a pyrazolotriazine (PT) base which is bound to the ribose or to the deoxyribose, as described herein, and is meant to encompass adenosine (in which the ribose sugar may be unmodified at the 2' position, i.e. 2'OH or modified at the 2' position, e.g. 2'OCH$_3$, 2'MOE and the like) or deoxyadenosine (in which the 2' position of the ribose sugar may be unmodified, i.e. 2'H or modified, e.g. 2'F and the like) pyrazolotriazine nucleotide analogues, respectively.

"Guanine PT nucleotide analogue" refers to a nucleotide in which the guanine base has been replaced with a pyrazolotriazine (PT) base which is bound to the ribose or to the deoxyribose, as described herein, and is meant to encompass guanosine (in which the ribose sugar may be unmodified at the 2' position, i.e. 2'OH or modified at the 2' position, e.g. 2'OCH$_3$, 2'MOE and the like) and deoxyguanosine (in which the 2' position of the ribose sugar may be unmodified, i.e. 2'H or modified, e.g. 2'F and the like) pyrazolotriazine nucleotide analogues, respectively.

TABLE 1

Adenine and Guanine PT nucleotide analogues of formulas Ia and Ib, respectively

Ia                Ib

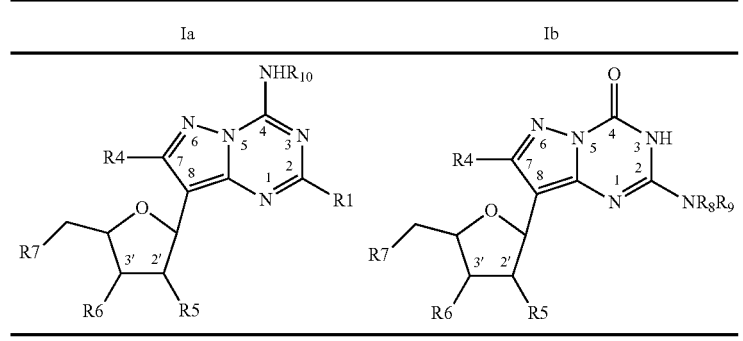

In certain more particular embodiments, the nucleoside analogue of the present invention is an adenine PT nucleotide analogue of the general formula Ia, i.e., a compound of the general formula I as defined above, wherein $R_1$ and $R_4$ each independently is H, halogen, ($C_1$-$C_2$)alkyl, —O—($C_1$-$C_2$)alkyl, —S—($C_1$-$C_2$)alkyl, —CO—H, —CO—($C_1$-$C_2$)alkyl, or —NR$_8$R$_9$, wherein $R_8$ and $R_9$ are each independently H, ($C_1$-$C_2$)alkyl, or an amine protecting group; $R_2$ is absent; $R_3$ is —NR$_{10}$R$_{10'}$, wherein $R_{10}$ and $R_{10'}$ are each independently H or an amine protecting group; $R_5$ is H, halogen, —O⁻, or —OR$_{11}$; $R_6$ is —O⁻, or —OR$_{11}$; $R_7$ is —OR$_{11}$, or a phosphate, preferably monophosphate, moiety; and $R_{11}$ each independently is H, ($C_1$-$C_4$)alkyl, ($C_1$-$C_4$)alkylene-OH, ($C_1$-$C_4$)alkylene-OCH$_3$, ($C_1$-$C_4$)alkylene-SH, ($C_1$-$C_4$)alkylene-SCH$_3$, ($C_1$-$C_4$)alkylene-NH$_2$, a hydroxyl protecting group, or —P(O-cyanoethyl)N(i-propyl)$_2$. Preferred such adenine PT nucleotide analogues are those wherein $R_5$ is H, halogen, —O⁻, or —OR$_{11}$; $R_6$ is —O⁻, or —OR$_{11}$; $R_7$ is —OR$_{11}$, or a monophosphate moiety; and $R_{11}$ each independently is H, ($C_1$-$C_2$)alkyl, ($C_1$-$C_2$)alkylene-OH, ($C_1$-$C_2$)alkylene-OCH$_3$, ($C_1$-$C_2$)alkylene-SH, ($C_1$-$C_2$)alkylene-SCH$_3$, ($C_1$-$C_2$)alkylene-NH$_2$, a hydroxyl protecting group, or —P(O-cyanoethyl)N(i-propyl)$_2$. More preferred such adenine PT nucleotide analogues are those wherein $R_1$ and $R_4$ are H; $R_3$ is —NR$_{10}$R$_{10'}$, wherein $R_{10}$ and $R_{10'}$ are each independently H or an amine protecting group; $R_5$ is H, halogen, —O⁻, or —OR$_{11}$; $R_6$ is —O⁻, or —OR$_{11}$; $R_7$ is —OR$_{11}$, or a monophosphate moiety; and $R_{11}$ each independently is H, ($C_1$-$C_2$)alkyl, ($C_1$-$C_2$)alkylene-OH, ($C_1$-$C_2$)alkylene-OCH$_3$, a hydroxyl protecting group, or —P(O-cyanoethyl)N(i-propyl)$_2$. The full chemical structures of specific such adenine PT nucleotide analogues described in the specification are depicted in Table 2 hereinafter.

In specific embodiments, the adenine PT nucleotide analogue of the invention is a compound of the general formula I, wherein (i) $R_1$ and $R_4$ are H; $R_2$ is absent; $R_3$ is —NR$_{10}$R$_{10'}$; $R_5$ is H; $R_6$ is —OH; $R_7$ is —OH; and $R_{10}$ and $R_{10'}$ are each independently H or benzoyl (compounds 14 and 15, respectively); (ii) $R_1$ and $R_4$ are H; $R_2$ is absent; $R_3$ is —NR$_{10}$R$_{10'}$; $R_5$ is H; $R_6$ is —OH; $R_7$ is —[O—PO$_3$]⁻, —[O—PO$_2$S]$^{2-}$, or —[O—PO$_2$(BH$_3$)]$^{2-}$; and $R_{10}$ and $R_{10'}$ are each independently H or benzoyl (compounds 16, 16a, 16b, 17, 17a and 17b, respectively); (iii) $R_1$ and $R_4$ are H; $R_2$ is absent; $R_3$ is —NR$_{10}$R$_{10'}$; $R_5$ is H; $R_6$ is —OR$_{11}$, wherein $R_{11}$ is —P(O-cyanoethyl)N(i-propyl)$_2$; $R_7$ is —OH; and $R_{10}$ and $R_{10'}$ are each independently H or benzoyl (compounds 18 and 19, respectively); (iv) $R_1$ and $R_4$ are H; $R_2$ is absent; $R_3$ is —NR$_{10}$R$_{10'}$; $R_5$ is H; $R_6$ is —OR$_{11}$, wherein $R_{11}$ is —P(O-cyanoethyl)N(i-propyl)$_2$; $R_7$ is —ODMT; and $R_{10}$ and $R_{10'}$ are each independently H or benzoyl (compounds 20 and 21, respectively); (v) $R_1$ and $R_4$ are H; $R_2$ is absent; $R_3$ is —NR$_{10}$R$_{10'}$; $R_5$ is —OH; $R_6$ is —OR$_{11}$, wherein $R_{11}$ is —P(O-cyanoethyl)N(i-propyl)$_2$; $R_7$ is —OH; and $R_{10}$ and $R_{10'}$ are each independently H or benzoyl (compounds 22 and 23, respectively); (vi) $R_1$ and $R_4$ are H; $R_2$ is absent; $R_3$ is —NR$_{10}$R$_{10'}$; $R_5$ is —OH; $R_6$ is —OR$_{11}$, wherein $R_{11}$ is —P(O-cyanoethyl)N(i-propyl)$_2$; $R_7$ is —ODMT; and $R_{10}$ and $R_{10'}$ are each independently H or benzoyl (compounds 24 and 25, respectively); (vii) $R_1$ and $R_4$ are H; $R_2$ is absent; $R_3$ is —NR$_{10}$R$_{10'}$; $R_5$ is —OR$_{11}$, wherein $R_{11}$ is —P(O-cyanoethyl)N(i-propyl)$_2$; $R_6$ is —OH; $R_7$ is —OH; and $R_{10}$ and $R_{10'}$ are each independently H or benzoyl (compounds 26 and 27, respectively); (viii) $R_1$ and $R_4$ are H; $R_2$ is absent; $R_3$ is —NR$_{10}$R$_{10'}$; $R_5$ is —OR$_{11}$, wherein $R_{11}$ is —P(O-cyanoethyl)N(i-propyl)$_2$; $R_6$ is —OH; $R_7$ is —ODMT; and $R_{10}$ and $R_{10'}$ are each independently H or benzoyl (compounds 28 and 29, respectively); (ix) $R_1$ and $R_4$ are H; $R_2$ is absent; $R_3$ is —NR$_{10}$R$_{10'}$; $R_5$ is —OCH$_3$; $R_6$ is —OH; $R_7$ is —OH; and $R_{10}$ and $R_{10'}$ are each independently H or benzoyl (compounds 30 and 31, respectively); (x) $R_1$ and $R_4$ are H; $R_2$ is absent; $R_3$ is —NR$_{10}$R$_{10'}$; $R_5$ is —OCH$_3$; $R_6$ is —OH; $R_7$ is —[O—PO$_3$]$^{2-}$, —[O—PO$_2$S]$^{2-}$, or —[O—PO$_2$(BH$_3$)]$^{2-}$; and $R_{10}$ and $R_{10'}$ are each independently H or benzoyl (compounds 32, 32a, 32b, 33, 33a and 33b, respectively); (xi) $R_1$ and $R_4$ are H; $R_2$ is absent; $R_3$ is —NR$_{10}$R$_{10'}$; $R_5$ is —OCH$_3$; $R_6$ is —OR$_{11}$, wherein $R_{11}$ is —P(O-cyanoethyl)N(i-propyl)$_2$; R$_7$ is —OH; and R$_{10}$ and R$_{10'}$ are each independently H or benzoyl (compounds 34 and 35, respectively); (xii) R$_1$ and R$_4$ are H; R$_2$ is absent; R$_3$ is —NR$_{10}$R$_{10'}$; R$_5$ is —OCH$_3$; R$_6$ is —OR$_{11}$, wherein R$_{11}$ is —P(O-cyanoethyl)N(i-propyl)$_2$; R$_7$ is —ODMT; and R$_{10}$ and R$_{10'}$ are each independently H or benzoyl (compounds 36 and 37, respectively); (xiii) R$_1$ and R$_4$ are H; R$_2$ is absent; R$_3$ is —NR$_{10}$R$_{10'}$; R$_5$ is —OR$_{11}$, wherein R$_{11}$ is —P(O-cyanoethyl)N(i-propyl)$_2$; R$_6$ is —OCH$_3$; R$_7$ is —OH; and R$_{10}$ and R$_{10'}$ are each independently H or benzoyl (compounds 38 and 39, respectively); (xiv) R$_1$ and R$_4$ are H; R$_2$ is absent; R$_3$ is —NR$_{10}$R$_{10'}$; R$_5$ is —OR$_{11}$, wherein R$_{11}$ is —P(O-cyanoethyl)N(i-propyl)$_2$; R$_6$ is —OCH$_3$; R$_7$ is —ODMT; and R$_{10}$ and R$_{10'}$ are each independently or benzoyl (compounds 40 and 41, respectively); (xv) R$_1$ and R$_4$ are H; R$_2$ is absent; R$_3$ is —NR$_{10}$R$_{10'}$; R$_5$ is —O(CH$_2$)$_2$—OCH$_3$; R$_6$ is —OH; R$_7$ is —OH; and R$_{10}$ and R$_{10'}$ are each independently H or benzoyl (herein identified compounds 42 and 43, respectively); (xvi) R$_1$ and R$_4$ are H; R$_2$ is absent; R$_3$ is —NR$_{10}$R$_{10'}$; R$_5$ is —O(CH$_2$)$_2$—OCH$_3$; R$_6$ is —OH; R$_7$ is —[O—PO$_3$]$^{2-}$, —[O—PO$_2$S]$^{2-}$, or —[O—PO$_2$(BH$_3$)]$^{2-}$; and R$_{10}$ and R$_{10'}$ are each independently H or benzoyl (herein identified compounds 44, 44a, 44b, 45, 45a and 45b, respectively); (xvii) R$_1$ and R$_4$ are H; R$_2$ is absent; R$_3$ is —NR$_{10}$R$_{10'}$; R$_5$ is —O(CH$_2$)$_2$—OCH$_3$; R$_6$ is —OR$_{11}$, wherein R$_{11}$ is —P(O-cyanoethyl)N(i-propyl)$_2$; R$_7$ is —OH; and R$_{10}$ and R$_{10'}$ are each independently H or benzoyl (herein identified compounds 46 and 47, respectively); (xviii) R$_1$ and R$_4$ are H; R$_2$ is absent; R$_3$ is —NR$_{10}$R$_{10'}$; R$_5$ is —O(CH$_2$)$_2$—OCH$_3$; R$_6$ is —OR$_{11}$, wherein R$_{11}$ is —P(O-cyanoethyl)N(i-propyl)$_2$; R$_7$ is —ODMT; and R$_{10}$ and R$_{10'}$ are each independently H or benzoyl (herein identified compounds 48 and 49, respectively); (xix) R$_1$ and R$_4$ are H; R$_2$ is absent; R$_3$ is —NR$_{10}$R$_{10'}$; R$_5$ is —OR$_{11}$, wherein R$_{11}$ is —P(O-cyanoethyl)N(i-propyl)$_2$; R$_6$ is —O(CH$_2$)$_2$—OCH$_3$; R$_7$ is —OH; and R$_{10}$ and R$_{10'}$ are each independently H or benzoyl (herein identified compounds 50 and 51, respectively); or (xx) R$_1$ and R$_4$ are H; R$_2$ is absent; R$_3$ is —NR$_{10}$R$_{10'}$; R$_5$ is —OR$_{11}$, wherein R$_{11}$ is —P(O-cyanoethyl)N(i-propyl)$_2$; R$_6$ is —O(CH$_2$)$_2$—OCH$_3$; R$_7$ is —ODMT; and R$_{10}$ and R$_{10'}$ are each independently H or benzoyl (herein identified compounds 52 and 53, respectively);

TABLE 2 specific adenine PT nucleotide analogues of the general formula I

| 14/15 | 16/17 |
|---|---|
| 14 (R$_{10}$ = H)<br>15 (R$_{10}$ = benzoyl) | 16 (R$_{10}$ = H)<br>17 (R$_{10}$ = benzoyl) |
| 18/19 | 20/21 |
| 18 (R$_{10}$ = H)<br>19 (R$_{10}$ = benzoyl) | 20 (R$_{10}$ = H)<br>21 (R$_{10}$ = benzoyl) |

TABLE 2-continued
specific adenine PT nucleotide analogues of the general formula I
| 22/23 | 24/25 |
|---|---|
| 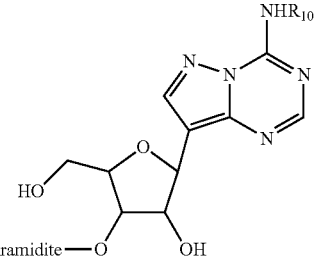<br>22 ($R_{10}$ = H)<br>23 ($R_{10}$ = benzoyl) | 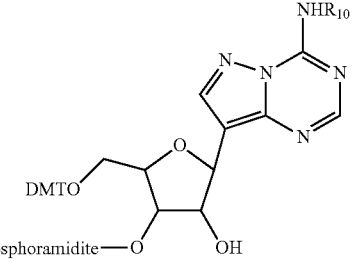<br>24 ($R_{10}$ = H)<br>25 ($R_{10}$ = benzoyl) |
| 26/27 | 28/29 |
| 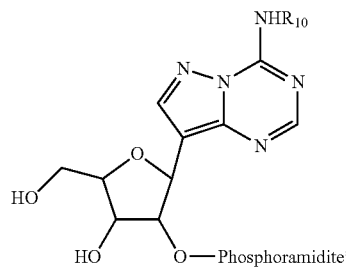<br>26 ($R_{10}$ = H)<br>27 ($R_{10}$ = benzoyl) | 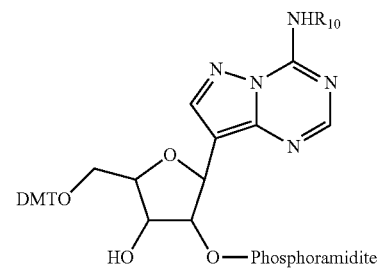<br>28 ($R_{10}$ = H)<br>29 ($R_{10}$ = benzoyl) |
| 30/31 | 32/33 |
| 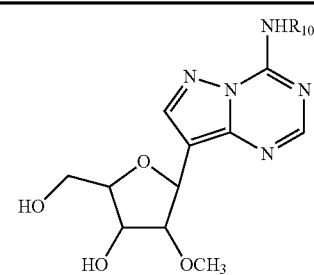<br>30 ($R_{10}$ = H)<br>31 ($R_{10}$ = benzoyl) | 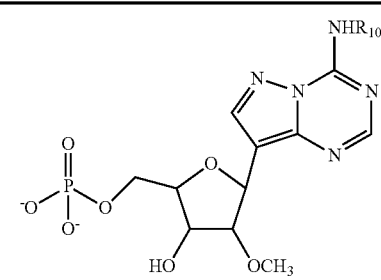<br>32 ($R_{10}$ = H)<br>33 ($R_{10}$ = benzoyl) |
| 34/35 | 36/37 |
| 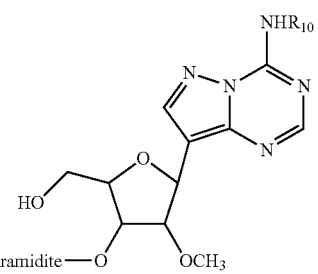<br>34 ($R_{10}$ = H)<br>35 ($R_{10}$ = benzoyl) | 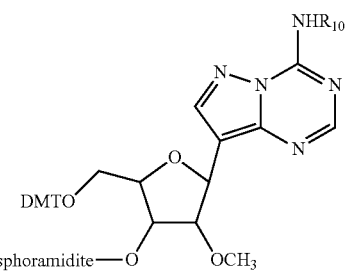<br>36 ($R_{10}$ = H)<br>37 ($R_{10}$ = benzoyl) |

TABLE 2-continued
specific adenine PT nucleotide analogues of the general formula I
| 38/39 | 40/41 |
|---|---|
| 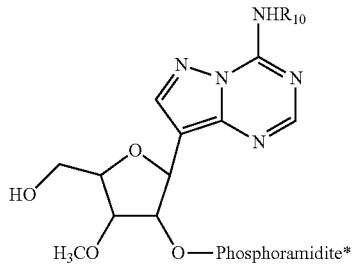<br>38 ($R_{10}$ = H)<br>39 ($R_{10}$ benzoyl) | 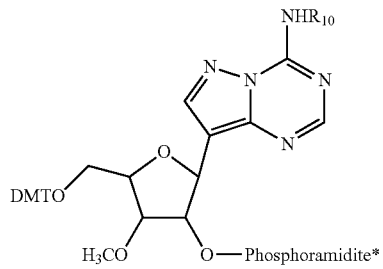<br>40 ($R_{10}$ = H)<br>41 ($R_{10}$ benzoyl) |
| 42/43 | 44/45 |
| 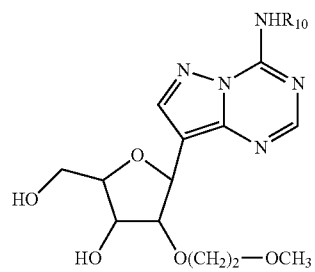<br>42 ($R_{10}$ = H)<br>43 ($R_{10}$ benzoyl) | 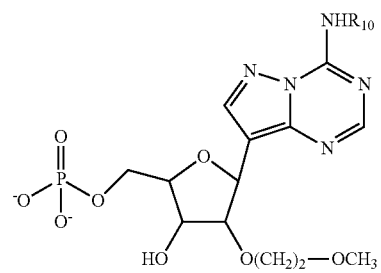<br>44 ($R_{10}$ = H)<br>45 ($R_{10}$ benzoyl) |
| 46/47 | 48/49 |
| 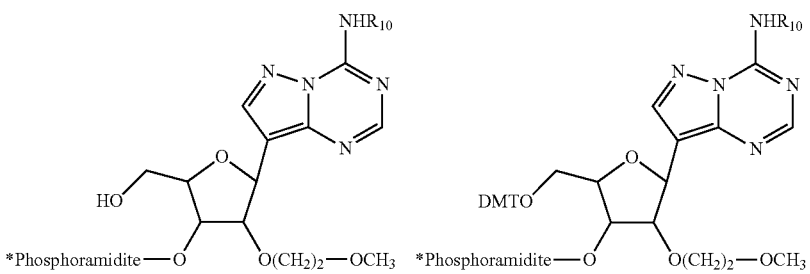<br>46 ($R_{10}$ = H)<br>47 ($R_{10}$ benzoyl) | 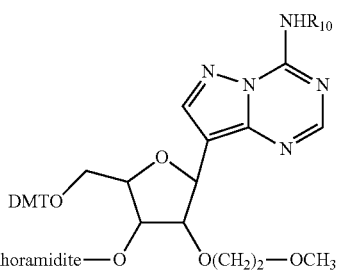<br>48 ($R_{10}$ = H)<br>49 ($R_{10}$ benzoyl) |

TABLE 2-continued specific adenine PT nucleotide analogues of the general formula I

| 50/51 | 52/53 |
|---|---|
| 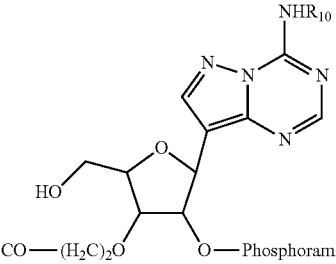 | 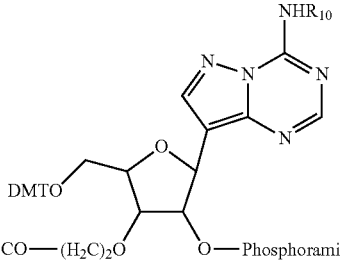 |
| 50 ($R_{10}$ = H) | 52 ($R_{10}$ = H) |
| 51 ($R_{10}$ = benzoyl) | 53 ($R_{10}$ = benzoyl) |

*The phosphoramidite moiety represents —P(O-cyanoethyl)N(i-propyl)$_2$.
**The Arabic numbers identifying those adenine PT nucleotide analogues in which the radical linked to the carbon atom at position 2' or 3' of the ribose, i.e., $R_5$ or $R_6$, respectively, is —OH, represent the corresponding analogues wherein $R_5$ or $R_6$, respectively, is —O$^-$ as well.
***Compounds 16a, 17a, 32a, 33a, 44a and 45a correspond to compounds 16, 17, 32, 33, 44 and 45, respectively, except for that $R_7$ is —[O—PO$_2$S]$^{2-}$ rather than —[O—PO$_3$]$^{2-}$. Compounds 16b, 17b, 32b, 33b, 44b and 45b correspond to compounds 16, 17, 32, 33, 44 and 45, respectively, except for that $R_7$ is —[O—PO$_2$(BH$_3$)]$^{2-}$ rather than —[O—PO$_3$]$^{2-}$.

In other more particular embodiments, the nucleoside analogue of the present invention is a guanine PT nucleotide analogue of the general formula Ib, i.e., a compound of the general formula I as defined above, wherein $R_1$ is —NR$_8$R$_9$, wherein $R_8$ and $R_9$ are each independently H or an amine protecting group; $R_2$ is H; $R_3$ is O; $R_4$ is H, halogen, ($C_1$-$C_2$)alkyl, —O—($C_1$-$C_2$)alkyl, —S—($C_1$-$C_2$)alkyl, —CO—H, —CO—($C_1$-$C_2$)alkyl, or —NR$_8$R$_9$, wherein $R_8$ and $R_9$ are each independently H, ($C_1$-$C_2$)alkyl, or an amine protecting group; $R_5$ is H, halogen, —O$^-$, or —OR$_{11}$; $R_6$ is —O$^-$, or —OR$_{11}$; $R_7$ is —OR$_{11}$, or a phosphate, preferably monophosphate, moiety; and $R_{11}$ each independently is H, ($C_1$-$C_4$)alkyl, ($C_1$-$C_4$)alkylene-OH, ($C_1$-$C_4$)alkylene-OCH$_3$, ($C_1$-$C_4$)alkylene-SH, ($C_1$-$C_4$)alkylene-SCH$_3$, ($C_1$-$C_4$)alkylene-NH$_2$, a hydroxyl protecting group, or —P(O-cyanoethyl) N(i-propyl)$_2$. In some embodiments the guanine PT nucleotide analogues are those wherein $R_5$ is H, halogen, —O$^-$, or —OR$_{11}$; $R_6$ is —O$^-$, or —OR$_{11}$; $R_7$ is —OR$_{11}$, or a monophosphate moiety; and $R_{11}$ each independently is H, ($C_1$-$C_2$)alkyl, ($C_1$-$C_2$)alkylene-OH, ($C_1$-$C_2$)alkylene-OCH$_3$, ($C_1$-$C_2$)alkylene-SH, ($C_1$-$C_2$)alkylene-SCH$_3$, ($C_1$-$C_2$)alkylene-NH$_2$, a hydroxyl protecting group, or —P(O-cyanoethyl) N(i-propyl)$_2$. In some other embodiments, the guanine PT nucleotide analogues are those wherein $R_1$ is —NR$_8$R$_9$, wherein $R_8$ and $R_9$ are H; $R_2$ is H; $R_3$ is O; $R_4$ is H; $R_5$ is H, halogen, —O$^-$, or —OR$_{11}$; $R_6$ is —O$^-$, or —OR$_{11}$; $R_7$ is —OR$_{11}$, or a monophosphate moiety; and $R_{11}$ each independently is H, ($C_1$-$C_2$)alkyl, ($C_1$-$C_2$)alkylene-OH, ($C_1$-$C_2$) alkylene-OCH$_3$, a hydroxyl protecting group, or —P(O-cyanoethyl)N(i-propyl)$_2$. The full chemical structures of such guanine PT nucleotide analogues described in the specification are depicted in Table 3 hereinafter.

In specific embodiments, the guanine PT nucleotide analogue of the invention is a compound of the general formula I, wherein (i) $R_1$ is —NHR$_9$; $R_2$ is H; $R_3$ is O; $R_4$ is H; $R_5$ is H; $R_6$ is —OH; $R_7$ is —OH; and $R_9$ is H or benzoyl (compounds 54 and 55, respectively); (ii) $R_1$ is —NHR$_9$; $R_2$ is H; $R_3$ is O; $R_4$ is H; $R_5$ is H; $R_6$ is —OH; $R_7$ is —[O—PO$_3$]$^{2-}$, —[O—PO$_2$S]$^{2-}$, or —[O—PO$_2$(BH$_3$)]$^{2-}$; and $R_9$ is H or benzoyl (compounds 56, 56a, 56b, 57, 57a and 57b, respectively); (iii) $R_1$ is —NHR$_9$; $R_2$ is H; $R_3$ is O; $R_4$ is H; $R_5$ is H; $R_6$ is —OR$_{11}$, wherein $R_{11}$ is —P(O-cyanoethyl)N(i-propyl)$_2$; $R_7$ is —OH; and $R_9$ is H or benzoyl (compounds 58 and 59, respectively); (iv) $R_1$ is —NHR$_9$; $R_2$ is H; $R_3$ is O; $R_4$ is H; $R_5$ is H; $R_6$ is —OR$_{11}$, wherein $R_{11}$ is —P(O-cyanoethyl)N(i-propyl)$_2$; $R_7$ is —ODMT; and $R_9$ is H or benzoyl (compounds 60 and 61, respectively); (v) $R_1$ is —NHR$_9$; $R_2$ is H; $R_3$ is O; $R_4$ is H; $R_5$ is —OH; $R_6$ is —OR$_{11}$, wherein $R_{11}$ is —P(O-cyanoethyl)N(i-propyl)$_2$; $R_7$ is —OH; and $R_9$ is H or benzoyl (compounds 62 and 63, respectively); (vi) $R_1$ is —NHR$_9$; $R_2$ is H; $R_3$ is O; $R_4$ is H; $R_5$ is —OH; $R_6$ is —OR$_{11}$, wherein $R_{11}$ is —P(O-cyanoethyl)N(i-propyl)$_2$; $R_7$ is —ODMT; and $R_9$ is H or benzoyl (compounds 64 and 65, respectively); (vii) $R_1$ is —NHR$_9$; $R_2$ is H; $R_3$ is O; $R_4$ is H; $R_5$ is —OR$_{11}$, wherein $R_{11}$ is —P(O-cyanoethyl)N(i-propyl)$_2$; $R_6$ is —OH; $R_7$ is —OH; and $R_9$ is H or benzoyl (compounds 66 and 67, respectively); (viii) $R_1$ is —NHR$_9$; $R_2$ is H; $R_3$ is O; $R_4$ is H; $R_5$ is —OR$_{11}$, wherein $R_{11}$ is —P(O-cyanoethyl)N(i-propyl)$_2$; $R_6$ is —OH; $R_7$ is —ODMT; and $R_9$ is H or benzoyl (compounds 68 and 69, respectively); (ix) $R_1$ is —NHR$_9$; $R_2$ is H; $R_3$ is O; $R_4$ is H; $R_5$ is —OCH$_3$; $R_6$ is —OH; $R_7$ is —OH; and $R_9$ is H or benzoyl (compounds 70 and 71, respectively); (x) $R_1$ is —NHR$_9$; $R_2$ is H; $R_3$ is O; $R_4$ is H; $R_5$ is —OCH$_3$; $R_6$ is —OH; $R_7$ is —[O—PO$_3$]$^{2-}$, —[O—PO$_2$S]$^{2-}$, or —[O—PO$_2$(BH$_3$)]$^{2-}$; and $R_9$ is H or benzoyl (compounds 72, 72a, 72b, 73, 73a and 73b, respectively); (xi) $R_1$ is —NHR$_9$; $R_2$ is H; $R_3$ is O; $R_4$ is H; $R_5$ is —OCH$_3$; $R_6$ is —OR$_{11}$, wherein $R_{11}$ is —P(O-cyanoethyl) N(i-propyl)$_2$; $R_7$ is —OH; and $R_9$ is H or benzoyl (compounds 74 and 75, respectively); (xii) $R_1$ is —NHR$_9$; $R_2$ is H; $R_3$ is O; $R_4$ is H; $R_5$ is —OCH$_3$; $R_6$ is —OR$_{11}$, wherein $R_{11}$ is —P(O-cyanoethyl)N(i-propyl)$_2$; $R_7$ is —ODMT; and $R_9$ is H or benzoyl (compounds 76 and 77, respectively); (xiii) $R_1$ is —NHR$_9$; $R_2$ is H; $R_3$ is O; $R_4$ is H; $R_5$ is —OR$_{11}$, wherein $R_{11}$ is —P(O-cyanoethyl)N(i-propyl)$_2$; $R_6$ is —OCH$_3$; $R_7$ is —OH; and $R_9$ is H or benzoyl (compounds 78 and 79, respectively); (xiv) $R_1$ is —NHR$_9$; $R_2$ is H; $R_3$ is O; $R_4$ is H; $R_5$ is —OR$_{11}$, wherein $R_{11}$ is —P(O-cyanoethyl) N(i-propyl)$_2$; $R_6$ is —OCH$_3$; $R_7$ is —ODMT; and $R_9$ is H or benzoyl (compounds 80 and 81, respectively); (xv) $R_1$ is —NHR$_9$; $R_2$ is H; $R_3$ is O; $R_4$ is H; $R_5$ is —O(CH$_2$)$_2$— OCH$_3$; $R_6$ is —OH; $R_7$ is —OH; and $R_9$ is H or benzoyl (herein identified compounds 82 and 83, respectively); (xvi)

R$_1$ is —NHR$_9$; R$_2$ is H; R$_3$ is O; R$_4$ is H; R$_5$ is —O(CH$_2$)$_2$—OCH$_3$; R$_6$ is —OH; R$_7$ is —[O—PO$_3$]$^{2-}$, —[O—PO$_2$S]$^{2-}$, or —[O—PO$_2$(BH$_3$)]$^{2-}$; and R$_9$ is H or benzoyl (herein identified compounds 84, 84a, 84b, 85, 85a and 85b, respectively); (xvii) R$_1$ is —NHR$_9$; R$_2$ is H; R$_3$ is O; R$_4$ is H; R$_5$ is —O(CH$_2$)$_2$—OCH$_3$; R$_6$ is —OR$_{11}$, wherein R$_{11}$ is —P(O-cyanoethyl)N(i-propyl)$_2$; R$_7$ is —OH; and R$_9$ is H or benzoyl (herein identified compounds 86 and 87, respectively); (xviii) R$_1$ is —NHR$_9$; R$_2$ is H; R$_3$ is O; R$_4$ is H; R$_5$ is —O(CH$_2$)$_2$—OCH$_3$; R$_6$ is —OR$_{11}$, wherein R$_{11}$ is —P(O-cyanoethyl)N(i-propyl)$_2$; R$_7$ is —ODMT; and R$_9$ is H or benzoyl (herein identified compounds 88 and 89, respectively); (xix) R$_1$ is —NHR$_9$; R$_2$ is H; R$_3$ is O; R$_4$ is H; R$_5$ is —OR$_{11}$, wherein R$_{11}$ is —P(O-cyanoethyl)N(i-propyl)$_2$; R$_6$ is —O(CH$_2$)$_2$—OCH$_3$; R$_7$ is —OH; and R$_9$ is H or benzoyl (herein identified compounds 90 and 91, respectively); or (xx) R$_1$ is —NHR$_9$; R$_2$ is H; R$_3$ is O; R$_4$ is H; R$_5$ is —OR$_{11}$, wherein R$_{11}$ is —P(O-cyanoethyl)N(i-propyl)$_2$; R$_6$ is —O(CH$_2$)$_2$—OCH$_3$; R$_7$ is —ODMT; and R$_9$ is H or benzoyl (herein identified compounds 92 and 93, respectively).

TABLE 3

Specific guanine PT nucleotide analogues of the general formula I

| 54/55 | 56/57 |
|---|---|
| 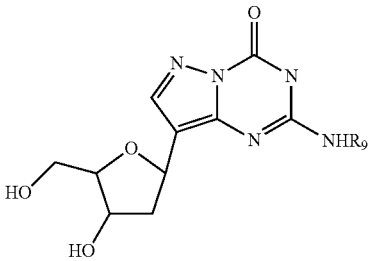<br>54 (R$_9$ = H)<br>55 (R$_9$ = benzoyl) | 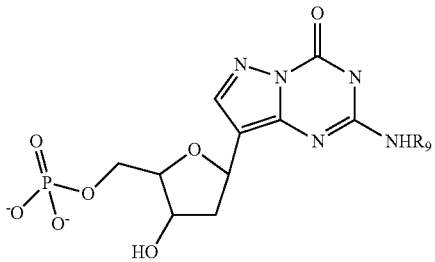<br>56 (R$_9$ = H)<br>57 (R$_9$ = benzoyl) |
| 58/59 | 60/61 |
| 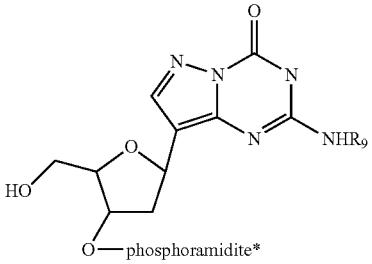<br>58 (R$_9$ = H)<br>59 (R$_9$ = benzoyl) | 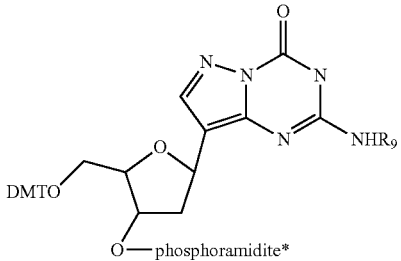<br>60 (R$_9$ = H)<br>61 (R$_9$ = benzoyl) |
| 62/63 | 64/65 |
| 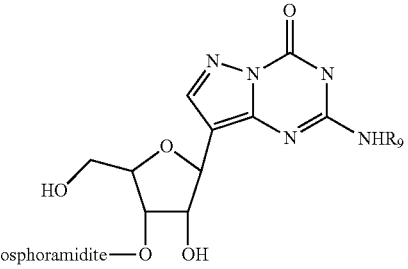<br>62 (R$_9$ = H)<br>63 (R$_9$ = benzoyl) | 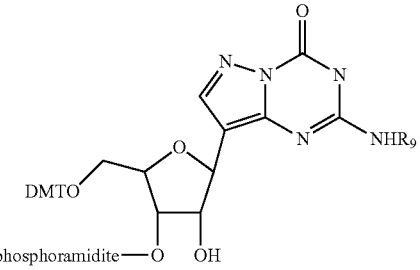<br>64 (R$_9$ = H)<br>65 (R$_9$ = benzoyl) |

TABLE 3-continued
Specific guanine PT nucleotide analogues of the general formula I
| 66/67 | 68/69 |
|---|---|
| 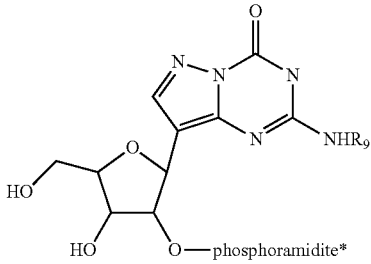<br>66 (R₉ = H)<br>67 (R₉ = benzoyl) | 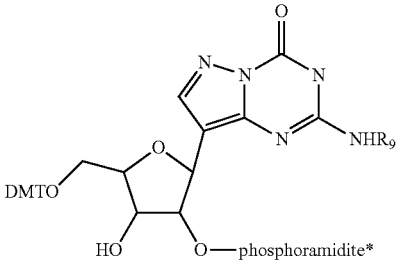<br>68 (R₉ = H)<br>69 (R₉ = benzoyl) |
| 70/71 | 72/73 |
| 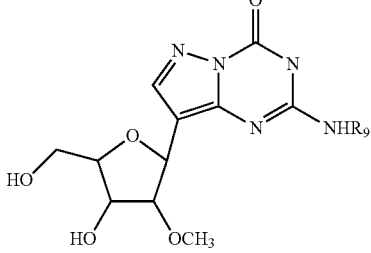<br>70 (R₉ = H)<br>71 (R₉ = benzoyl) | 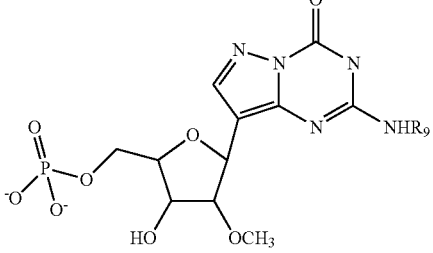<br>72 (R₉ = H)<br>73 (R₉ = benzoyl) |
| 74/75 | 76/77 |
| 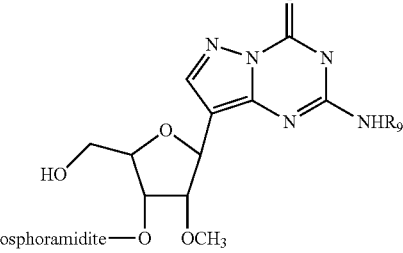<br>74 (R₉ = H)<br>75 (R₉ = benzoyl) | 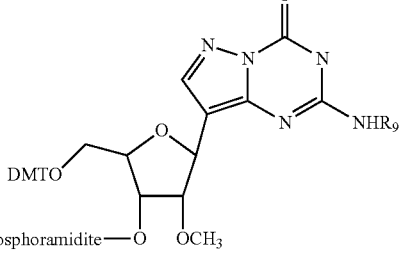<br>76 (R₉ = H)<br>77 (R₉ = benzoyl) |
| 78/79 | 80/81 |
| 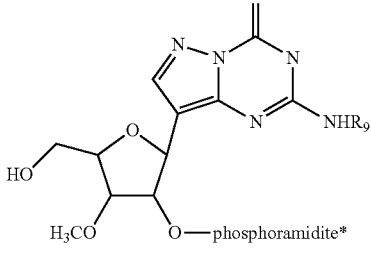<br>78 (R₉ = H)<br>79 (R₉ = benzoyl) | 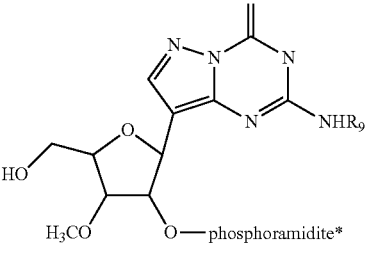<br>80 (R₉ = H)<br>81 (R₉ = benzoyl) |

TABLE 3-continued

Specific guanine PT nucleotide analogues of the general formula I

| 82/83 | 84/85 |
|---|---|
| 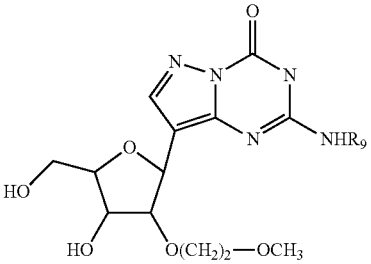 82 ($R_9$ = H)<br>83 ($R_9$ = benzoyl) | 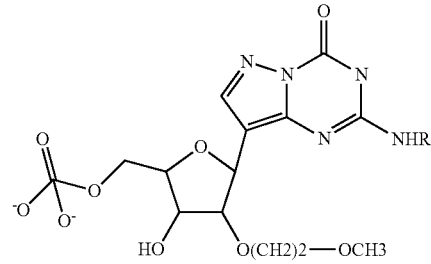 84 ($R_9$ = H)<br>85 ($R_9$ = benzoyl) |
| 86/87 | 88/89 |
| 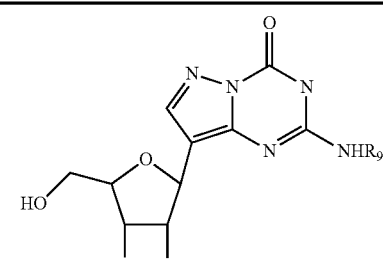 86 ($R_9$ = H)<br>87 ($R_9$ = benzoyl) | 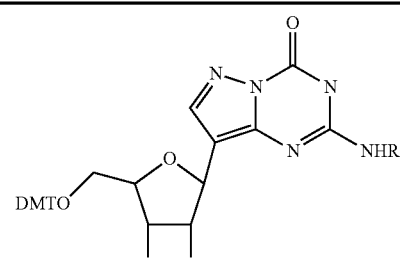 88 ($R_9$ = H)<br>89 ($R_9$ = benzoyl) |
| 90/91 | 92/93 |
| 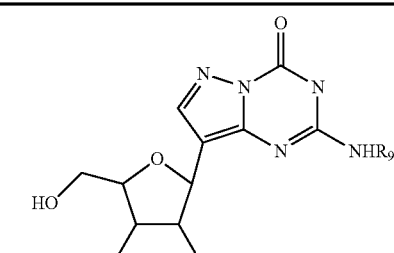 90 ($R_9$ = H)<br>91 ($R_9$ = benzoyl) | 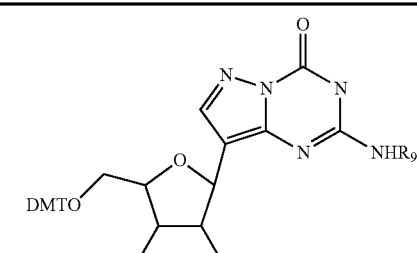 92 ($R_9$ = H)<br>93 ($R_9$ = benzoyl) |

*The phosphoramidite moiety represents —P(O-cyanoethyl)N(i-propyl)$_2$.
**The Arabic numbers identifying those guanine PT nucleotide analogues in which the radical linked to the carbon atom at position 2' or 3' of the ribose, i.e., $R_5$ or $R_6$, respectively, is —OH, represent the corresponding analogues wherein $R_5$ or $R_6$, respectively, is —O⁻ as well.
***Compounds 56a, 57a, 72a, 73a, 84a and 85a correspond to compounds 56, 57, 72, 73, 84 and 85, respectively, except for that $R_7$ is —[O—PO$_2$S]$^{2-}$ rather than —[O—PO$_3$]$^{2-}$. Compounds 56b, 57b, 72b, 73b, 84b and 85b correspond to compounds 56, 57, 72, 73, 84 and 85, respectively, except for that $R_7$ is —[O—PO$_2$(BH$_3$)]$^{2-}$ rather than —[O—PO$_3$]$^{2-}$.

The various nucleoside analogues of the present invention may be synthesized according to any suitable technology or procedure known in the art, e.g., as described in the Examples section hereinafter.

As shown in the Examples section with respect to the adenine PT nucleotide analogue herein identified as compound 21, the nucleoside analogues of the present invention can be incorporated into oligonucleotides, substituting natural purine nucleosides and imparting acid and nuclease stability to the oligonucleotide. Furthermore, oligonucleotides comprising one or more such nucleoside analogues are capable, in terms of stability and specificity, of hybridizing with oligonucleotides having complementary sequences thereto in which no such analogues are incorporated.

In another aspect, the present invention provides an oligonucleotide as defined above, comprising at least one, i.e., one or more, nucleoside analogues each independently of the general formula I.

The key step in DNA synthesis is the specific and sequential formation of internucleotide phosphate linkages. Since a deoxyribonucleoside monomer contains two hydroxyl groups (3' and 5' or alternatively 2' and 5'), one must be chemically protected while the other is specifically phosphorylated or phosphitylated, and then coupled to the next deoxyribonucleoside unit. Meanwhile, other reactive moieties, e.g., exo-cyclic amino groups, must also be protected.

The phosphotriester methods of DNA synthesis in solution require coupling of one appropriately protected monomer unit containing a 3'- or 2'-phosphate with another containing a 5'-hydroxyl group and separation of products and unreacted starting materials on a column of silica gel.

Synthesis of oligonucleotides by the solid-phase method brings advantages of speed, micro-scale operation, labor reduction and ease of mechanization. In essence, the method involves attachment of a 3' (or alternatively 2') or 5'-O-protected ribonucleoside or deoxyribonucleoside to a solid support and chain assembly by alternating terminal 3' (or alternatively 2') or 5'-deprotection reactions (type 1) and coupling reactions (type 2). In both cases, excess reagent is added to drive the reaction to completion and unreacted components are removed merely by washing of the support with an appropriate solvent. Cycles of synthesis are continued until the required length is obtained and then the oligonucleotide is cleaved from the support, protecting groups are removed, and the deprotected oligonucleotide is purified.

High-throughput DNA synthesis is normally done by the phosphoramidite four-step process. Now, a novel two-step cycle (Dellinger et al., 2005), enables a higher purity DNA to be obtained in a less costly way.

New discoveries, such as siRNA, have driven the scientific community to develop synthetic methods for RNA as efficiently as DNA. Thanks to the development of new reagents, the classical RNA synthesis using a 2'-O-tertbutyldimethylsilyl protecting group has reached the level of 99% coupling yields (Sproat, 2005). New methods have also been developed in the field of RNA synthesis. One of these methods uses an inverse protection scheme (acid labile group in the 2'-O-position and fluoride labile group in the 5' 0-position) (Hartsel et al., 2005). Using this method, the oligonucleotide remains in its 2'-O-protected form until final deprotection is carried out before use.

The most widely used oligonucleotides in antisense technology are phosphorothioates, to protect the antisense from nucleases including cleavage by RNase H.

Although the phosphoramidite approach has become the method of choice for oligonucleotide synthesis, the H-phosphonate alternative remains a useful alternative, especially for solution-phase synthesis and when only a small excess of building block are used (Stawinski and Stromberg, 2005). The original phosphotriester approach to oligonucleotide synthesis has no longer routine application, but is still very useful, e.g., for the ring closure of circular oligonucleotides. The synthesis of circular oligonucleotides is described by Pedroso et al., (2005), who points to the many potential applications of circular DNA.

In certain embodiments, the present invention provides an oligonucleotide as defined above, wherein $R_1$ and $R_4$ in each one of said one or more nucleoside analogues each independently is H, halogen, —CN, —SCN, —NO$_2$, —O-hydrocarbyl, —S— hydrocarbyl, —CO—H, —CO-hydrocarbyl, —NR$_8$R$_9$, heteroaryl, or hydrocarbyl, wherein $R_8$ and $R_9$ are each independently H or hydrocarbyl; and said hydrocarbyl each independently is $(C_1$-$C_8)$alkyl, preferably $(C_1$-$C_4)$alkyl, more preferably $(C_1$-$C_2)$alkyl. In particular such embodiments, $R_1$ and $R_4$ in each one of said one or more nucleoside analogues each independently is H, halogen, —O-hydrocarbyl, —S— hydrocarbyl, —CO—H, —CO-hydrocarbyl, —NR$_8$R$_9$, heteroaryl, or hydrocarbyl, wherein $R_8$ and $R_9$ are each independently H or hydrocarbyl; and said hydrocarbyl each independently is $(C_1$-$C_4)$alkyl, preferably $(C_1$-$C_2)$alkyl.

In certain embodiments, the present invention provides an oligonucleotide as defined above, wherein $R_3$ in each one of said one or more nucleoside analogues independently is O or —NR$_{10}$R$_{10'}$, wherein $R_{10}$ and $R_{10'}$ are each independently H, hydrocarbyl, or —CO-hydrocarbyl; and said hydrocarbyl is $(C_1$-$C_8)$alkyl, preferably $(C_1$-$C_4)$alkyl, more preferably $(C_1$-$C_2)$alkyl.

In certain embodiments, the present invention provides an oligonucleotide as defined above, wherein $R_5$ in each one of said one or more nucleoside analogues is H, halogen, —O$^-$, or —OR$_{11}$, wherein $R_{11}$ is H, $(C_1$-$C_4)$alkyl, preferably $(C_1$-$C_2)$alkyl, $(C_1$-$C_4)$alkylene-OR$_{12}$, preferably $(C_1$-$C_2)$alkylene-OR$_{12}$, $(C_1$-$C_4)$alkylene-SR$_{12}$, preferably $(C_1$-$C_2)$alkylene-SR$_{12}$, or $(C_1$-$C_4)$alkylene-NR$_{12}$R$_{13}$, preferably $(C_1$-$C_2)$alkylene-NR$_{12}$R$_{13}$; and $R_{12}$ and $R_{13}$ each independently is H or $(C_1$-$C_4)$alkyl, preferably $(C_1$-$C_2)$alkyl. In particular such embodiments, $R_5$ in each one of said one or more nucleoside analogues is H, halogen, —O$^-$, or —OR$_{11}$, wherein $R_{11}$ is H, $(C_1$-$C_2)$alkyl, $(C_1$-$C_2)$alkylene-OH, $(C_1$-$C_2)$alkylene-OCH$_3$, $(C_1$-$C_2)$alkylene-SH, $(C_1$-$C_2)$alkylene-SCH$_3$, or $(C_1$-$C_2)$alkylene-NH$_2$.

In certain embodiments, the present invention provides an oligonucleotide as defined above, wherein $R_6$ in each one of said one or more nucleoside analogues is —O$^-$, or —OR$_{11}$, wherein $R_{11}$ is H, $(C_1$-$C_4)$alkyl, preferably $(C_1$-$C_2)$alkyl, $(C_1$-$C_4)$alkylene-OR$_{12}$, preferably $(C_1$-$C_2)$alkylene-OR$_{12}$, $(C_1$-$C_4)$alkylene-SR$_{12}$, preferably $(C_1$-$C_2)$alkylene-SR$_{12}$, or $(C_1$-$C_4)$alkylene-NR$_{12}$R$_{13}$, preferably $(C_1$-$C_2)$alkylene-NR$_{12}$R$_{13}$; and $R_{12}$ and $R_{13}$ each independently is H or $(C_1$-$C_4)$alkyl, preferably $(C_1$-$C_2)$alkyl. In particular such embodiments, $R_6$ in each one of said one or more nucleoside analogues is —O$^-$, or —OR$_{11}$, wherein $R_{11}$ is H, $(C_1$-$C_2)$alkyl, $(C_1$-$C_2)$alkylene-OH, $(C_1$-$C_2)$alkylene-OCH$_3$, $(C_1$-$C_2)$alkylene-SH, $(C_1$-$C_2)$alkylene-SCH$_3$, or $(C_1$-$C_2)$alkylene-NH$_2$.

In particular embodiments, the present invention provides an oligonucleotide as defined above, wherein in each one of said one or more nucleoside analogues: (i) $R_1$ and $R_4$ each independently is H, halogen, $(C_1$-$C_4)$alkyl, —O—$(C_1$-$C_4)$alkyl, —S—$(C_1$-$C_4)$alkyl, —CO—H, —CO—$(C_1$-$C_4)$alkyl, or —NR$_8$R$_9$, wherein $R_8$ and $R_9$ are each independently H or $(C_1$-$C_4)$alkyl; (ii) $R_3$ independently is O or —NR$_{10}$R$_{10'}$, wherein $R_{10}$ and $R_{10'}$ are each independently H, $(C_1$-$C_4)$alkyl, or —CO—$(C_1$-$C_4)$alkyl; (iii) $R_5$ independently is H, halogen, —O$^-$, or —OR$_{11}$; (iv) $R_6$ independently is —O$^-$ or —OR$_{11}$; and (v) $R_{11}$ each independently is H, $(C_1$-$C_2)$alkyl, $(C_1$-$C_2)$alkylene-OH, $(C_1$-$C_2)$alkylene-OCH$_3$, $(C_1$-$C_2)$alkylene-SH, $(C_1$-$C_2)$alkylene-SCH$_3$, or $(C_1$-$C_2)$alkylene-NH$_2$. In more particular embodiments, the invention provides such an oligonucleotide, wherein in each one of said one or more nucleoside analogues: (i) $R_1$ and $R_4$ each independently is H, halogen, $(C_1$-$C_2)$alkyl, —O—$(C_1$-$C_2)$alkyl, —S—$(C_1$-$C_2)$alkyl, —CO—H, —CO—$(C_1$-$C_2)$alkyl, or —NR$_8$R$_9$, wherein $R_8$ and $R_9$ are each independently H or $(C_1$-$C_2)$alkyl; and (ii) $R_3$ independently is O or —NR$_{10}$R$_{10'}$, wherein $R_{10}$ and $R_{10'}$ are each independently H, $(C_1$-$C_2)$ alkyl, or —CO—$(C_1$-$C_2)$alkyl.

In certain embodiments, the oligonucleotide of the present invention comprises at least one, e.g., 1, 2, 3, 4, 5, 6, 7, 8, 9, 10, 11, 12, 13, 14, 15 or more, nucleoside analogues each independently of the general formula II, wherein $R_2$ is absent; and $R_3$ is —NR$_{10}$R$_{10'}$ as defined above, i.e., at least one adenine PT nucleotide analogue. In other embodiments, the oligonucleotide of the invention comprises at least one, e.g., 1, 2, 3, 4, 5, 6, 7, 8, 9, 10, 11, 12, 13, 14, 15 or more, nucleoside analogues each independently of the general formula II, wherein $R_1$ is —$NR_8R_9$ as defined above; $R_2$ is H; and $R_3$ is O, i.e., at least one guanine PT nucleotide analogue. In further embodiments, the oligonucleotide of the invention comprises at least one adenine PT nucleotide analogue as defined above and at least one guanine PT nucleotide analogue as defined above.

Oligonucleotide synthesis is commonly performed from the 3' terminus to the 5' terminus (3'→5') or from the 5' terminus to the 3' terminus (5'→3'). Nevertheless, as stated above, the nucleoside analogues of the general formula I, more particularly, ribonucleoside analogues wherein the radical linked to the carbon atom at the 2' position of the ribose moiety, i.e., $R_5$, is —O⁻ or —$OR_{11}$, can be incorporated into the oligonucleotide synthesized involving 2'→5' or 5'→2' attachment as well. It should thus be understood that each one of said one or more nucleoside analogues comprised within the oligonucleotide of the present invention, whether it is an adenine PT nucleotide analogue substituting a natural adenosine or a guanine PT nucleotide analogue substituting a natural guanosine, may be located within the sequence of said oligonucleotide as well as at the 3'-2'- or 5'-terminus of said oligonucleotide. Consequently, in any one of said one or more nucleoside analogues incorporated within the oligonucleotide sequence, either the radical linked to the carbon atom at position 3' of the ribose moiety, i.e., $R_6$, or the radical linked to the carbon atom at position 2' of the ribose moiety, i.e., $R_5$, is —O⁻; and the group linked to the carbon atom at position 5' of the ribose moiety, i.e., $R_7$, is a phosphate linking moiety as defined above, in some embodiments, —[O—$PO_2$]⁻—, —[O—POS]⁻—, or —[O—PO($BH_3$)]⁻—, more preferably —[O—$PO_2$]⁻—. Contrary to that, in case a nucleoside analogue is located at the 3' terminus of said oligonucleotide (when synthesized 3'→5' or 5'→3') or at the 2' terminus of said oligonucleotide (when synthesized 2'→5' or 5'→2'), the radical linked to the carbon atom at position 3' or 2', respectively, of the ribose moiety in said nucleoside analogue may also be —$OR_{11}$, wherein $R_{11}$ is H, ($C_1$-$C_8$)alkyl, ($C_1$-$C_8$)alkylene-$OR_{12}$, ($C_1$-$C_8$)alkylene-$SR_{12}$, or ($C_1$-$C_8$)alkylene-$NR_{12}R_{13}$, wherein $R_{12}$ and $R_{13}$ each independently is H or ($C_1$-$C_8$)alkyl. Similarly, in case a nucleoside analogue is located at the 5' terminus of said oligonucleotide, the group linked to the carbon atom at position 5' of the ribose moiety of said nucleoside analogue may also be —$OR_{11}$, or a monophosphate moiety as defined above, wherein $R_{11}$ is H, ($C_1$-$C_8$)alkyl, ($C_1$-$C_8$)alkylene-$OR_{12}$, ($C_1$-$C_8$)alkylene-$SR_{12}$, or ($C_1$-$C_8$)alkylene-$NR_{12}R_{13}$, wherein $R_{12}$ and $R_{13}$ each independently is H or ($C_1$-$C_8$)alkyl.

In certain embodiments, the present invention provides an oligonucleotide as defined above, wherein (i) in each one of said one or more nucleoside analogues $R_5$ is —$OR_{11}$, and $R_6$ is —O⁻; (ii) in each one of said one or more nucleoside analogues $R_5$ is —O⁻, and $R_6$ is —$OR_{11}$; or (iii) in at least one of said one or more nucleoside analogues $R_5$ is —$OR_{11}$, and $R_6$ is —O⁻; and in at least one of said one or more nucleoside analogues $R_5$ is —O⁻, and $R_6$ is —$OR_{11}$.

In certain particular embodiments, the oligonucleotide of the present invention comprises one or more adenine PT nucleotide analogues each independently of the general formula II, wherein $R_1$ and $R_4$ each independently is H, halogen, ($C_1$-$C_2$)alkyl, —O—($C_1$-$C_2$)alkyl, —S—($C_1$-$C_2$)alkyl, —CO—H, —CO—($C_1$-$C_2$)alkyl, or —$NR_8R_9$, wherein $R_8$ and $R_9$ are each independently H or ($C_1$-$C_2$)alkyl; $R_2$ is absent; $R_3$ is —$NH_2$; $R_5$ is H, halogen, —O⁻, or —$OR_{11}$; $R_6$ is —O⁻, or —$OR_{11}$; $R_7$ is —$OR_{11}$, a monophosphate moiety, or a phosphate linking moiety; and $R_{11}$ each independently is H, ($C_1$-$C_4$)alkyl, ($C_1$-$C_4$)alkylene-OH, ($C_1$-$C_4$)alkylene-$OCH_3$, ($C_1$-$C_4$)alkylene-SH, ($C_1$-$C_4$)alkylene-$SCH_3$, or ($C_1$-$C_4$)alkylene-$NH_2$. In some embodiments, said oligonucleotide comprises one or more adenine PT nucleotide analogues each independently of the general formula II, wherein $R_5$ is H, halogen, —O⁻, or —$OR_{11}$; $R_6$ is —O⁻ or —$OR_{11}$; $R_7$ is —$OR_{11}$, a monophosphate moiety, or a phosphate linking moiety; and $R_{11}$ each independently is H, ($C_1$-$C_2$)alkyl, ($C_1$-$C_2$)alkylene-OH, ($C_1$-$C_2$)alkylene-$OCH_3$, ($C_1$-$C_2$)alkylene-SH, ($C_1$-$C_2$)alkylene-$SCH_3$, or ($C_1$-$C_2$)alkylene-$NH_2$.

In some embodiments about 5, 10, 20, 30, 40, 50, 60, 70, 80, 90 or 100% of the adenine bases in a sequence may be replaced by adenine PT nucleotide analogues.

Particular such adenine PT nucleotide analogues that may be incorporated within an oligonucleotide according to the present invention include, e.g., compounds of the general formula II, wherein $R_1$ and $R_4$ are H; $R_2$ is absent; $R_3$ is —$NH_2$; $R_5$ is H, —O⁻, —OH, or —$OCH_3$; $R_6$ is —O⁻ or —OH; and $R_7$ is —OH, —[O—$PO_3$]²⁻, —[O—$PO_2$S]²⁻, —[O—$PO_2(BH_3)$]²⁻, —[O—$PO_2$]⁻—, —[O—POS]⁻—, or —[O—PO($BH_3$)]⁻—.

In other particular embodiments, the oligonucleotide of the present invention comprises one or more guanine PT nucleotide analogues each independently of the general formula II, wherein $R_1$ is —$NH_2$; $R_2$ is H; $R_3$ is O; $R_4$ is H, halogen, ($C_1$-$C_2$)alkyl, —O—($C_1$-$C_2$)alkyl, —S—($C_1$-$C_2$)alkyl, —CO—H, —CO—($C_1$-$C_2$)alkyl, or —$NR_8R_9$, wherein $R_8$ and $R_9$ are each independently H or ($C_1$-$C_2$)alkyl, preferably H; $R_5$ is H, halogen, —O⁻, or —$OR_{11}$; $R_6$ is —O⁻, or —$OR_{11}$; $R_7$ is —$OR_{11}$, a monophosphate moiety, or a phosphate linking moiety; and $R_{11}$ each independently is H, ($C_1$-$C_4$)alkyl, ($C_1$-$C_4$)alkylene-OH, ($C_1$-$C_4$)alkylene-$OCH_3$, ($C_1$-$C_4$)alkylene-SH, ($C_1$-$C_4$)alkylene-$SCH_3$, or ($C_1$-$C_4$)alkylene-$NH_2$. In some embodiments, said oligonucleotide comprises one or more guanine PT nucleotide analogues each independently of the general formula II, wherein $R_5$ is H, halogen, —O⁻, or —$OR_{11}$; $R_6$ is —O⁻, or —$OR_{11}$; $R_7$ is —$OR_{11}$, a monophosphate moiety, or a phosphate linking moiety; and $R_{11}$ each independently is H, ($C_1$-$C_2$)alkyl, ($C_1$-$C_2$)alkylene-OH, ($C_1$-$C_2$)alkylene-$OCH_3$, ($C_1$-$C_2$)alkylene-SH, ($C_1$-$C_2$)alkylene-$SCH_3$, or ($C_1$-$C_2$)alkylene-$NH_2$.

In some embodiments about 5, 10, 20, 30, 40, 50, 60, 70, 80, 90 or 100% of the guanine bases in a sequence may be replaced by guanine PT nucleotide analogues.

Particular such guanine PT nucleotide analogues that may be incorporated within an oligonucleotide according to the present invention include, e.g., compounds of the general formula II, wherein $R_1$ is —$NH_2$; $R_2$ is H; $R_3$ is O; $R_4$ is H; $R_5$ is H, —O⁻, —OH, or —$OCH_3$; $R_6$ is —O⁻, or —OH; and $R_7$ is —OH, —[O—$PO_3$]²⁻, —[O—$PO_2$S]²⁻, —[O—$PO_2(BH_3)$]²⁻, —[O—$PO_2$]⁻—, —[O—POS]⁻—, or —[O—PO($BH_3$)]⁻—.

In one particular aspect, the invention provides an oligonucleotide as defined above, comprising one or more nucleoside analogues, more particularly deoxyribonucleoside analogues, each independently of the general formula II, wherein $R_5$ is H or halogen; $R_6$ is —O⁻ or —$OR_{11}$; and $R_{11}$ is H, ($C_1$-$C_8$)alkyl, ($C_1$-$C_8$)alkylene-$OR_{12}$, ($C_1$-$C_8$)alkylene-$SR_{12}$, or ($C_1$-$C_8$)alkylene-$NR_{12}R_{13}$, wherein $R_{12}$ and $R_{13}$ each independently is H or ($C_1$-$C_8$)alkyl, i.e., a DNA oligonucleotide.

In another particular aspect, the present invention provides an oligonucleotide as defined above, comprising one or more nucleoside analogues, more particularly ribonucleoside analogues, each independently of the general formula II, wherein $R_5$ is —O⁻, —OR$_{11}$; $R_6$ is —O⁻ or —OR$_{11}$; and $R_{11}$ each independently is H, (C$_1$-C$_8$)alkyl, (C$_1$-C$_8$)alkylene-OR$_{12}$, (C$_1$-C$_8$)alkylene-SR$_{12}$, or (C$_1$-C$_8$)alkylene-NR$_{12}$R$_{13}$, preferably H, wherein $R_{12}$ and $R_{13}$ each independently is H or (C$_1$-C$_8$)alkyl, i.e., an RNA oligonucleotide. According to the present invention, each one of said one or more ribonucleoside analogues can independently be incorporated into said RNA oligonucleotide via phosphodiester bonds involving either 2'→5' or 3'→5' attachment. In other words, in more particular such aspects, the invention provides such an RNA oligonucleotide, wherein (i) in each one of said one or more nucleoside analogues $R_5$ is —OR$_{11}$, and $R_6$ is —O⁻; (ii) in each one of said one or more nucleoside analogues $R_5$ is —O⁻, and $R_6$ is —OR$_{11}$; or (iii) in at least one of said one or more nucleoside analogues $R_5$ is —OR$_{11}$, and $R_6$ is —O⁻; and in at least one of said one or more nucleoside analogues $R_5$ is —O⁻, and $R_6$ is —OR$_{11}$.

The oligonucleotides of the present invention are either a DNA oligonucleotide as defined above or an RNA oligonucleotide as defined above, comprising two or more nucleotides. Such oligonucleotides may comprise, e.g., a sequence of 2-10, 2-20, 2-30, 2-40, 2-50, 2-60, 2-70, 2-80, 2-90 or 2-100 nucleotides, or in some embodiments are oligonucleotides comprising a sequence of up to 50 nucleotides, e.g., a sequence of from 10, 15, 20 or 25 to 50 nucleotides.

The term nucleotide as used herein refers to nucleotides derived from nucleoside analogues of the general formula I, as defined above, as well as to other deoxyribonucleotides or ribonucleotides that may be natural or synthetic and modified or unmodified. Naturally occurring bases include adenine, guanine, cytosine, thymine and uracil. Modified bases of nucleotides include, without being limited to, inosine, xanthine, hypoxanthine, 2-aminoadenine, 6-methyl, 2-propyl and other alkyl adenines, 5-halouracil, 5-halocytosine, 6-azacytosine and 6-az thymine, pseudouracil, deoxypseudouracil, 4-thiouracil, ribo-2-thiouridine, ribo-4-thiouridine, 8-haloadenine, 8-aminoadenine, 8-thioladenine, 8-thiolalkyl adenines, 8-hydroxyl adenine and other 8-substituted adenines, 8-haloguanines, 8-aminoguanine, 8-thiolguanine, 8-thioalkylguanines 8-hydroxylguanine and other substituted guanines, other aza and deaza adenines, other aza and deaza guanines, 5-methylribouridine, 5-trifluoromethyl uracil, 5-methylribocytosine, and 5-trifluorocytosine.

Examples of nucleotide analogues that may be incorporated within an oligonucleotide of the present invention include, without being limited to, phosphorothioates, phosphoramidites, methyl phosphonates, chiral-methyl phosphonates, 2'-O-methyl ribonucleotides (2'-OMe sugar modified), and peptide-nucleic acids (PNAs). Modifications include changes to the ribose moiety, the base moiety and or the linkages between ribonucleotides in the oligoribonucleotide. As used herein, the term "ribonucleotide" encompasses natural and synthetic, unmodified and modified ribonucleotides and ribonucleotide analogues which are synthetic, naturally occurring, and non-naturally occurring, wherein modifications include changes to the ribose moiety, to the base moiety and/or to the linkages between ribonucleotides in the oligonucleotide.

A ribose modification includes a modification on the 2' moiety of the ribose moiety and encompasses amino, fluoro, alkoxy, e.g., methoxy and ethoxy, alkyl, amino, fluoro, chloro, bromo, CN, CF, imidazole, carboxylate, thioate, unsubstituted and substituted (C$_1$-C$_{10}$)alkyl, alkaryl or aralkyl, OCF$_3$, OCN, O—, S—, or N-alkyl; O—, S—, or N-alkenyl; SOCH$_3$; SO$_2$CH$_3$; ONO$_2$; NO$_2$, N$_3$; heterocycloalkyl; heterocycloalkaryl; amino alkyl amino; polyalkylamino or substituted silyl, as, among others, described in European patents EP 0586520B1 or EP 0618925 B1.

In a further aspect, the present invention provides a double-stranded DNA molecule, wherein at least one strand is a DNA oligonucleotide as defined above. In one particular aspect, the invention provides a double-stranded DNA molecule, wherein one of the two strands is a DNA oligonucleotide as defined above; and in another particular aspect, the invention provides a double-stranded DNA molecule, wherein both strands are a DNA oligonucleotide as defined above.

According to the present invention, each one of the nucleotides comprised within each one of the strands of the double-stranded DNA, i.e., both nucleotides derived from nucleoside analogues of the general formula I as well as all other nucleotides, is a deoxyribonucleotide. Other double-stranded nucleic acid molecules based on the oligonucleotides of the present invention, including siRNA molecules, are disclosed in U.S. Provisional Application No. 61/653,432 entitled: "Therapeutic oligonucleotides comprising nucleotide analogues", filed on the same date and to be assigned to the assignee of the present application and to QBI Enterprises Ltd., Israel.

The nucleoside analogues of the general formula II can be incorporated into oligonucleotides as defined above to generate chemically modified ssDNA, dsDNA, ssRNA or their analogues, opening the development of DNA or RNA-based strategies such as: catalytic ribozyme or DNAzyme that can be synthesized with the capacity to bind and cleave mRNA or viral genomic RNA. Antisense RNA or DNA can also be prepared to target RNA including mRNA or viral genomic RNA, and sterically block translation or induce mRNA degradation by the non-specific endonuclease RNAse H. The nucleoside analogues of the general formula II can also be introduced into ssDNA or ssRNA-aptamers to specifically bind a variety of selected targets with high affinity. The nucleoside analogues of the general formula I can further be utilized in the preparation of immunostimulatory CpG oligonucleotides to activate the immune system by detection of bacterial products.

The oligonucleotides of the present invention can particularly be useful in the Antisense Therapeutics Approach; indeed, when purine bases (A and G) of a particular sequence are partially or fully replaced by pyrazolotriazoyl-based nucleoside analogues (dA$^{PT}$ and dG$^{PT}$, also termed herein pA and pG, respectively), an improved stability of these oligomers in acidic conditions, especially into the endosomal compartments, should result in a significant inhibition or activation of gene expression into the targeted cells. This effect will be reinforced when additional 5', 3' and/or internal modifications such as phosphorothioate linkages can be added to the oligomers, protecting the antisense oligonucleotide against nucleases and acidic effects. Oligonucleotides which include a combination of, e.g., modified linkages and the nucleoside analogues disclosed herein should exhibit a dramatic increase in the half-life of the resulting antisense oligonucleotide into the cells, leading to a more efficient gene modulation.

The oligonucleotides of the present invention are powerful tools in antisense technology because: (i) substitution of natural purine nucleosides with pA or pG into these oligonucleotides doesn't destabilize the duplex formed with the RNA targets including mRNA targets; (ii) they are capable of activating RNAse H; (iii) they are fully specific to their targets will result in non toxicity effects, making them highly interested for antisense therapeutics applications; and (iv)

they improve cellular uptake. Typical methods used for encapsulating antisense oligonucleotides in lipid vesicles result in very low encapsulation efficiencies at neutral pH, due to the polyanionic structures of the macromolecules. Antisense-oligonucleotides according to the present invention will allow encapsulation in more acidic conditions, and therefore will help to increase the process efficiency, resulting in improved pharmacokinetics of the formulation.

In still another aspect, the present invention provides a pharmaceutical composition comprising a nucleoside analogue of the general formula I as defined above, and a pharmaceutically acceptable carrier.

In yet another aspect, the present invention provides a pharmaceutical composition comprising a DNA oligonucleotide as defined above; or an RNA oligonucleotide as defined above; or a double-stranded DNA molecule as defined above, and a pharmaceutically acceptable carrier.

A multitude of delivery agents can be included like the electrical and mechanical strategies, viral or nonviral delivery system, polymeric delivery system—like lipoplex or cationic polymer, polyethyleneimine (PEI)—a branched polymer with high cationic potential, poly(L-lysine)—a biodegradable cationic polymer, chitosan—a natural biodegradable polymer, dendrimers—polycationic synthetic polymer, and liposomal delivery systems. These delivery agents can be associated with targeting ligands to enhance the cellular uptake of oligonucleotide-based therapeutics. In these particular aspects, peptides ligands, transferrin—a larger protein ligand, antibodies and aptamers can be used.

In still a further aspect, the present invention thus provides an expression vector comprising a double-stranded DNA molecule as defined above.

In yet a further aspect, the present invention relates to a method for reducing gene expression in a cell comprising transfecting said cell with an oligonucleotide as defined above, or with an expression vector as defined above.

The invention will now be illustrated by the following non-limiting Examples.

EXAMPLES

Example 1: Synthesis of 8-[3'-(2-cyanoethyl)-(N,N-diisopropyl)]-phosphoramidite-(2'-deoxy-5'-dimethoxytrityl-β-D-ribofuranozyl)-4-(N-benzoylamino)-pyrazolo[1,5a]-1,3,5-triazine, 21

The C-nucleoside analogue 21 containing a pyrazolo[1,5a]-1,3,5-triazine ring as adenine mimic was synthesized using a multi-step procedure.

Figure 4:
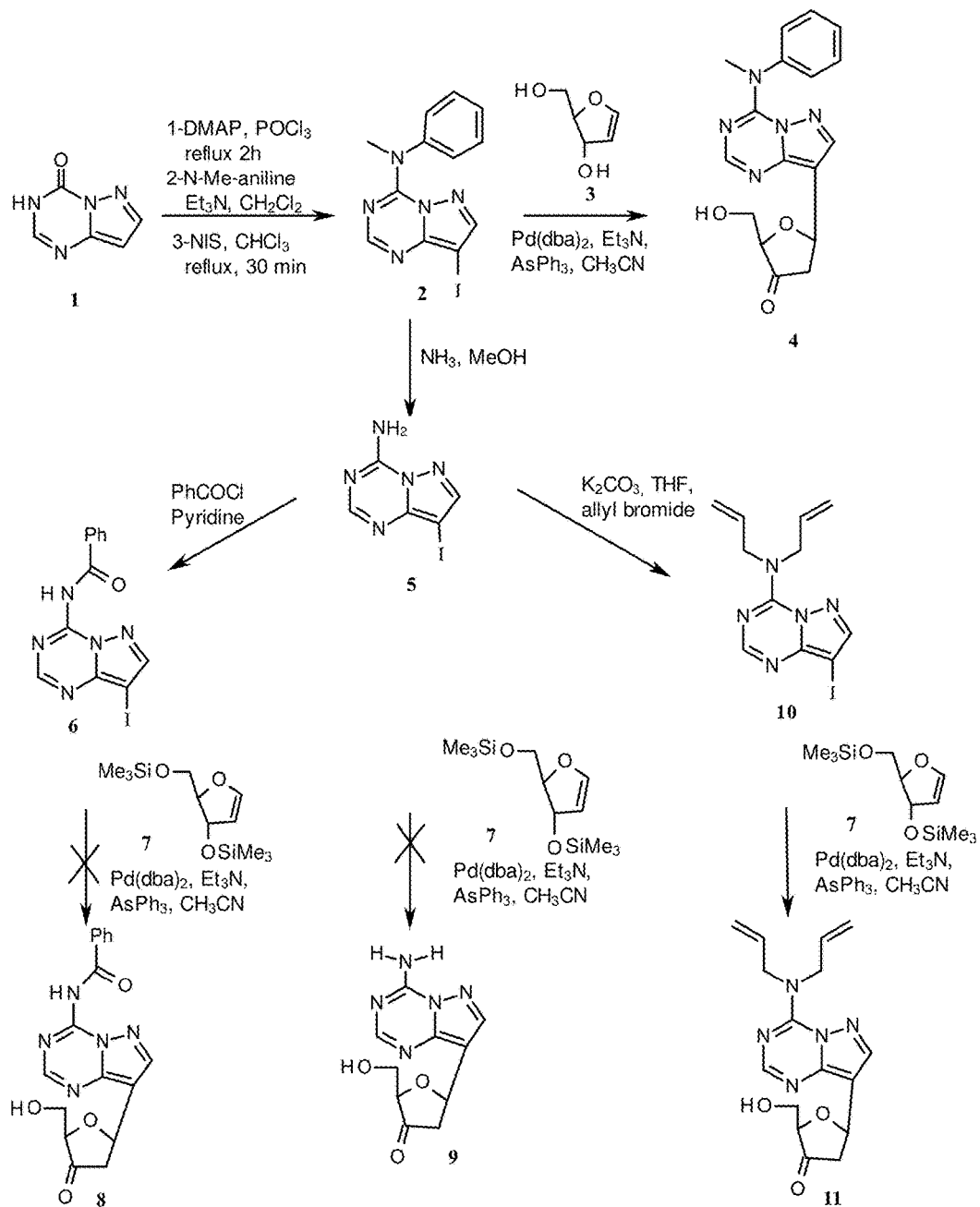
FIG. 4 shows the influence of the protective group on the 4-amino function of the nucleic base analogue on the formation of the C—C glycosidic bond.

As depicted in FIG. 4, based on the results described by Daves (Arai and Daves, 1978; Daves, 1990), and a further research including that recently reported by Raboisson et al. (2002) describing the use of N-methyl,N-phenylamino as protective groups for the amino substituent in position 4 of an iodo-aglycon, the first target of this multi-step synthesis was the preparation of 8-iodo-3H-pyrazolo[1,5a]-1,3,5-triazine-4-N-methyl-phenyl amine 2 from the previously reported 3H-pyrazolo[1,5a]-1,3,5-triazine-4-one, 1 (Chu et al., 1980). This was achieved by a known three-step synthetic path, in which 1 was reacted with phosphorus oxychloride in the presence of dimethylaminopyridine (DMAP), followed by reaction with N-methylaniline (Raboisson et al., 2002) and then treatment with N-iodosuccinimide (NIS) to give the iodopyrazolotriazine 2 in about 73% overall yield.

The Heck coupling reaction (Daves, 1990) between the aglycon 2 and the unprotected glycal 3 (easily obtained from thymidine as described by Larsen et al., 1994) was used for the first time ever to successfully give the keto compound 4 in 34% yield, using bis-(dibenzylidene acetone) palladium$^0$, triphenyl arsine and triethylamine in acetonitrile around reflux.

The iodo-pyrazolo[1,5a]-1,3,5-triazine derivative 2 was initially used as nucleic base in further coupling reactions. But N-methyl,N-phenylamino protective groups have been reported moderately suitable only for nucleophilic addition-elimination displacement in the position 4 of C-nucleoside analogues (Raboisson et al., 2002). Therefore, the conversion to the amino group during deprotection step by ammonia treatment, upon oligonucleotide synthesis, was not compatible with the incorporation of more than one dA-like nucleoside. Many attempts to achieve suitable coupling reactions with iodo-pyrazolo[1,5a]-1,3,5-triazine derivative 2 using either the 4-unprotected nucleic base analogue or different other protection groups such as benzoyl and bis-benzoyl (Schaller et al., 1963), or allyl and bis-allyl (Hayakawa et al., 1990), even with a bis-protected glycal proved to be unpractical.

Figure 5:
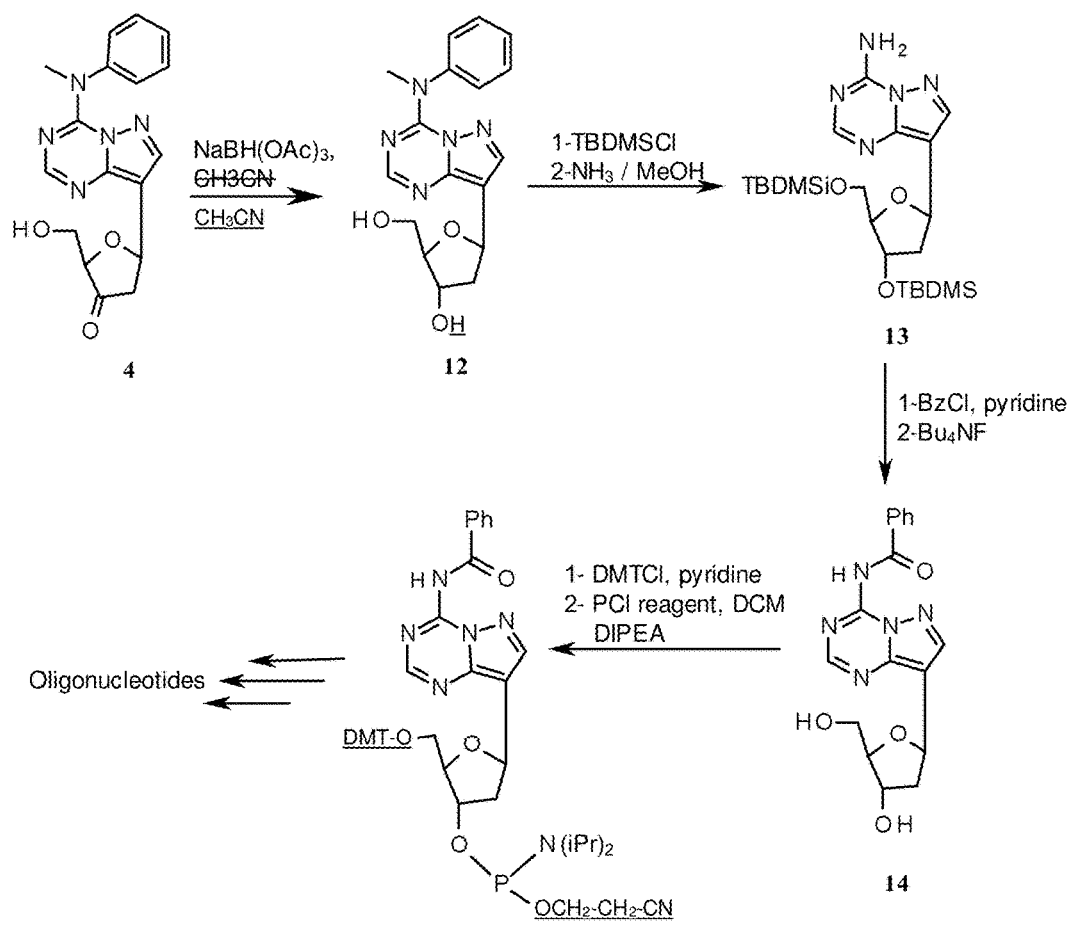
FIG. 5 shows synthesis of the deoxy adenine (dA) pyrazolotriazine nucleotide analogue phosphoramidite.

These results led the idea to keep the existing protection of the amino group at the nucleoside level and to use the keto-derivative 4 instead of the nucleic base 2, as depicted in FIG. 5. In particular, the 3'-carbonyl group reduction of 4, performed using sodium-triacetoxy borohydride in acetonitrile, gave the new nucleoside 12 in 89% yield. Tert-butyldimethylsilyl chloride was then used to protect the 3' and 5'-hydroxyl groups of the glycal ring in 12, while the free 4-amino group was obtained by treatment with methanolic-ammonia to give the new compound 13 in a 55% yield. The deprotection of the 3' and 5' hydroxyl groups in 13 required first the reprotection of the 4-amino function using benzoyl chloride in pyridine and then desilylation using tetrabutyl ammonium fluoride to give the new nucleoside 14 in 73% yield. Selective primary 5'-hydroxyl group protection of 14 was achieved by treatment with 4,4'-dimethoxytrityl chloride and then treatment with 2-cyanoethyl-N,N-diisopropylchlorophosphite introduced the corresponding cyanatophosphite ester in the 3' position to give the new phosphoramidite nucleoside 21 in 31% yield.

Preparation of 8-(2'-deoxy-β-D-glycero-pentofuran-3'-ulos-1'-yl)-4-(N-methyl-N-phenylamino)-pyrazolo[1,5a]-1,3,5-triazine, 4

A solution of bis(dibenzylideneacetone)palladium$^0$ (1.94 mmol, 0.06 eq., 1.12 g) and triphenyl arsine (3.88 mmol, 0.12 eq., 1.19 g) in acetonitrile (200 ml) was stirred at room temperature (RT) for 1 hr and was then added to a solution of iodo-pyrazolotriazine, 2 (30.96 mmol, 1 eq., 10.87 g) prepared as previously described (Chu et al., 1980), crude glycal, 3 (61.92 mmol, 2 eq., 1.12 g), and triethylamine (33.15 mmol, 1.2 eq., 5.18 ml) in acetonitrile (300 ml). The mixture was stirred at 82° C. for 16 hr, cooled and worked up to a brown residue which is purified by chromatography (eluent: PE/EA 5050) to give a brown solid. Yield: 1.7 g, 16%.

Molecular formula: $C_{17}H_{17}N_5O_3$; MW=339.36 g/mol; M.P.: 157-158° C.; $[\alpha]D^{20}$=+1.46 (c=1, chloroform). The structure was fully confirmed by $^1H$ and $^{13}C$-NMR; IR and MS (CI): m/z=340 [MH$^+$].

Preparation of 8-(2'-deoxy-β-D-ribofuranozyl)-4-(N-methyl-N-phenylamino)-pyrazolo[1,5a]-1,3,5-triazine, 12

Sodium tri(acetoxy)borohydride (19.92 mmol, 4 eq., 4.22 g) was added in aliquots to solution of the keto derivative 4

(4.98 mmol, 1 eq., 1.69 g) in acetonitrile (60 ml) at RT, and was then stirred at RT for 5 hr. The mixture was hydrolysed and the solvent was then evaporated. The residue was purified by chromatography (eluent: DCM/MeOH 955) to give a white solid. Yield: 1.16 g, 68%.

Molecular formula: $C_{17}H_{19}N_5O_3$; MW=341.37 g/mol; M.P.: 196-198° C. (dec.); $[\alpha]D^{20}$=+4.2 (c=1, DMF). The structure was fully confirmed by $^1$H and $^{13}$C-NMR; IR and MS (CI): m/z=364 [M+Na].

Preparation of 8-[(2'-deoxy-3',5'-di(tert-butyl-dimethylsilyl)-β-D-ribofuranozyl]-4-(N-methyl-N-phenylamino)-pyrazolo[1,5a]-1,3,5-triazine, 12A Tert-butyldimethylsilyl chloride (21.27 mmol, 6 eq., 3.2 g) was added to solution of the unprotected ribofuranozyl-pyrazolotriazine compound 12 (3.54 mmol, 1 eq., 1.21 g) and imidazole (42.53 mmol, 12 eq., 2.89 g) in DMF (25 ml) at RT, and was then stirred at RT for 60 hr. The solvent is evaporated and the crude product is purified by chromatography (eluent: PE/EA 982) to give a yellow oil. Yield: 1.43 g, 71%.

Molecular formula: $C_{29}H_{47}N_5O_3\ Si_2$; MW=569.9 g/mol; M.P.: 94-95° C.; $[\alpha]D^{20}$=–18.0 (c=1, chloroform). The structure was fully confirmed by $^1$H and $^{13}$C-NMR; IR and MS (CI): m/z=571 [MH]$^+$.

Preparation of 8-[(2'-deoxy-3',5'-di(tert-butyl-dimethylsilyl)-β-D-ribofuranozyl]-4-aminopyrazolo[1,5a]-1,3,5-triazine, 13

A solution of ammonia in methanol, 7N, (28 mmol, 11.2 eq., 4 ml) was added to solution of the protected ribofuranozyl-pyrazolotriazine compound 12A (2.5 mmol, 1 eq., 1.43 g) in methanol (50 ml) contained in a sealable tube. The charged tube was sealed and the mixture is stirred at 100° C. for 19 hr. The solvent was evaporated upon cooling and the crude product was purified by chromatography (eluent: PE/EA 9010) to give upon evaporation a white solid. Yield: 0.92 g, 77%.

Molecular formula: $C_{22}H_{41}N_5O_3\ Si_2$; MW=479.78 g/mol; M.P.: 126-128° C.; $[\alpha]D^{20}$=–1.5 (c=1, chloroform). The structure was fully confirmed by $^1$H and $^{13}$C-NMR; IR and MS (CI): m/z=480 [MH]$^+$.

Preparation of 8-[(2'-deoxy-3',5'-di(tert-butyl-dimethylsilyl)-β-D-ribofuranozyl]-4-(N-benzoylamino)-pyrazolo[1,5a]-1,3,5-triazine, 13A Benzoyl chloride (10.32 mmol, 5 eq., 1.2 ml) was added drop wise to solution of the ribofuranozyl-amino-pyrazolotriazine compound 13 (2.06 mmol, 1 eq., 0.99 g) in pyridine (11 ml) cooled at 0° C. The mixture was then stirred at RT for about 2 hr and was cooled again at 0° C. Water (10 ml) and then ammonium hydroxide (15 ml) were added drop wise and the solution was stirred at RT for 50 min. The solvent was evaporated. Water was added and the crude residue was extracted with DCM (2×50 ml). The layers were separated, the combined organic phase was dried, DCM evaporated and the crude product was purified by chromatography (eluent: PE/EA 9010) to give upon evaporation a white solid. Yield: 0.92 g, 80%.

Molecular formula: $C_{29}H_{45}N_5O_4\ Si_2$; MW=583.89 g/mol; M.P.: 70-72° C.; $[\alpha]D^{20}$=–10.8 (c=1, chloroform). The structure was fully confirmed by $^1$H and $^{13}$C-NMR (The Noesy experiment confirmed the β-configuration); IR and MS (CI): m/z=584 [MH]$^+$.

Preparation of 8-(2'-deoxy-3',5-β-D-ribofuranozyl)-4-(N-benzoylamino)-pyrazolo[1,5a]-1,3,5-triazine, 14

A solution of tetrabutyl ammonium fluoride 1M, (1.3 mmol, 3 eq., 1.3 ml) in THF was added to solution of the protected nucleoside compound 13A (1.45 mmol, 1 eq., 0.261 g) in THF (3 ml) at RT and was then stirred at RT for 6 hr. The solvent was evaporated and the crude product was purified by chromatography (eluent: DCM/MeOH 955) to give a white solid. Yield: 0.127 g, 80%.

Molecular formula: $C_{17}H_{17}N_5O_4$; MW=355.36 g/mol; M.P.: 144-145° C.; The structure was fully confirmed by $^1$H and $^{13}$C-NMR; IR and MS (Ions spray): m/z=356 [M+H]; 378 [M+Na].

Preparation of 8-(2'-deoxy-5'-dimethoxytrityl-fl-D-ribofuranozyl)-4-(N-benzoylamino)-pyrazolo[1,5a]-1,3,5-triazine, 14A The free-nucleoside 7(14) (1.66 mmol, 1 eq., 0.591 g) was dissolved under argon in dry pyridine (10 ml) and cooled to 0° C. A solution of dimethoxytrityl chloride (1.83 mmol, 1.1 eq., 0.62 g) in dry pyridine (10 ml) was then drop wise added over 1 hr to the cooled solution above. The mixture was then stirred at RT for 18 hr. The solvent was evaporated, water was added to the residue and mixture extracted with DCM (2×15 ml), washed with brine, dried and DCM evaporated. The crude product was purified by chromatography (eluent: DCM/MeOH 982) to give a white solid. Yield: 0.655 g, 60%.

Molecular formula: $C_{38}H_{35}N_5O_6$; MW=657.73 g/mol; M.P.: 118-120° C.; $[\alpha]D^{20}$=–10.1 (c=1, chloroform). The structure was fully confirmed by $^1$H and $^{13}$C-NMR.

Preparation of 8-[3'-(2-cyanoethyl)-(N,N-diisopropyl)]-phosphoramidite-(2'-deoxy-5'-dimethoxytrityl-β-D-ribofuranozyl)-4-(N-benzoylamino)-pyrazolo[1,5a]-1,3,5-triazine, 21

The tritylated-nucleoside 14A, (0.26 mmol, 1 eq., 0.144 g) and DCI 0.25 M, (0.17 mmol, 0.67 eq., 0.68 ml) were dissolved under argon in dry, freshly distilled DCM (2 ml). The PCl-reagent (0.31 mmol, 1.2 eq., 0.009 ml) was then added drop wise and the mixture was stirred at RT for 1 hr. Crushed ice was added for hydrolysis and the mixture was rapidly extracted with DCM (2×15 ml), the combined organic phase washed with cold brine, dried and DCM evaporated. The crude product was purified by chromatography (eluent: pentane/EA/Et$_3$N 60/39/1) to give a white solid. Yield: 0.133 g, 60%.

Molecular formula: $C_{47}H_{52}N_7O_7P$; MW=857.95 g/mol. The structure was fully confirmed by $^1$H; $^{13}$C-NMR and $^{31}$P-NMR; IR and MS (turbo spray): m/z=856.4 [M–H].

Example 2: Synthesis of Ribo-Pyrazolotriazine Adenosine Phosphoramidite, 111

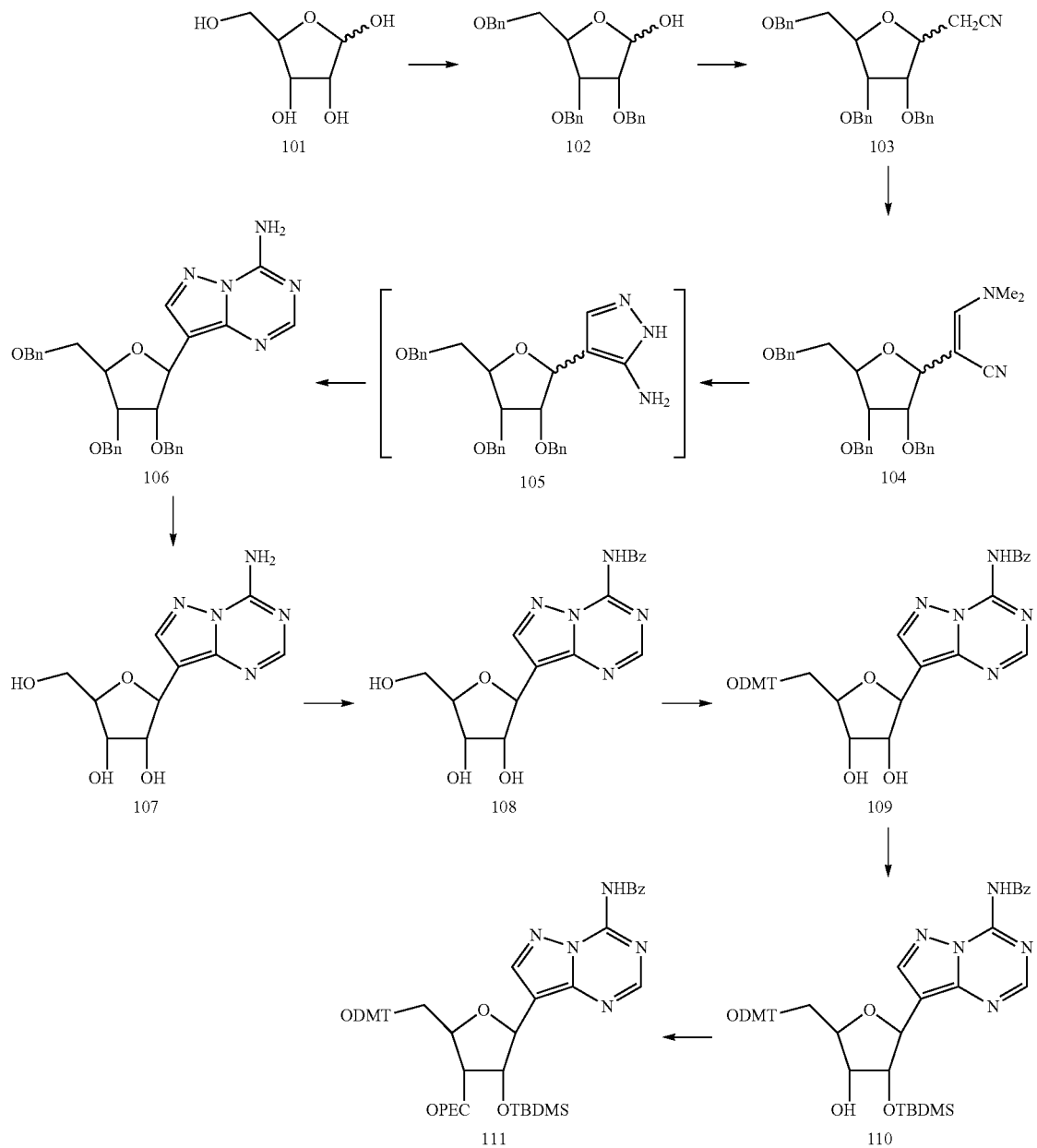

Step 1a: D-Ribose (1 gr) and 1M HCl, were agitated together in Methanol (100 ml), at 25° C. for 6-10 hours. Toluene (5 L) and DMF (5 L) are added and the mixture is evaporated under reduced pressure. Crude product is purified by CC (silica, DCM/MeOH as eluent).

Step 1b: Sodium Hydride (8 gr, 60% in mineral oil) is added to dry DMF (1.5 L) and the mixture is cooled. Then, the solution of product 101a in DMF is added keeping the temperature at about 5° C. Benzyl bromide (300 gr) is added keeping the temperature at about 5° C. The reaction mixture is warmed and maintained at this temperature. Then the solution is washed with DCM/water. The organic phase is evaporated under reduced pressure, to give crude compound 101b. Crude product is purified by CC (silica, DCM/MeOH as eluent).

Step 2: Product 101bis dissolved in about 0.5 L acetone. Then, about 0.1 L of water and 0.3 L of HCl 32% are added and the solution is warmed for about 6 hours. Working up is performed with Toluene/water. Solvent is evaporated, to give crude compound 102. Crude product is purified by CC (silica, DCM/MeOH as eluent).

Step 3: Compound 102: 2',3',5'-O-tribenzyl-β-D-ribofuranose, is dissolved in 70 mL of THF, NaH 60% in oil (17 gr) is added. Diethyl cyanomethylphosphonate (75 gr) is added slowly. Working up is performed using Toluene and water. Solvent is evaporated to give crude compound 103. Crude product is purified by CC (silica, EtAc/Hex as eluent).

Step 4: Compound 103: 2',3',5'-O-tribenzyl-b-D-ribofuranosylacetonitrile (1.15 gr) is dissolved in THF (15 mL) tert-Butoxybis(dimethylamino)methane (1.5 gr) is added; the solution is warmed and stirred overnight. Working up is performed with Hexane and water. Solvent is evaporated, to give crude compound 104. Crude product is purified by CC (silica, EtAc/Hex as eluent).

NMR $^1$H (CDCl$_3$, 250 MHz): 3.04 (s, 6H, N(CH$_3$)$_2$), 3.45-3.59 (ddd, 2H, H-5, J=4.9 Hz, 10.3 Hz, 18.8 Hz), 3.90-4.00 (m, 2H, H-2 and H-3), 4.14-4.18 (m, 1H, H-4), 4.31 (d, 1H, H-1, J=7.0 Hz), 4.53-4.61 (m, 6H, CH$_2$Ph), 6.47 (s, 1H, CH=), 7.26-7.33 (m, 15H, 3×Ph).

Step 5: Compound 104: 3-Dimethylamino-2-(2',3',5'-O-tribenzyl-b-D-ribofuranosyl)acrylonitrile (795 mg) is dissolved in 2 mL Pyridine. Hydrazine (242 mg) is added; and reaction mixture is warmed for about 16 hours. Working up is performed with Toluene water to give compound 105.

Step 6: Compound 105: 4-(2',3',5'-O-tribenzyl-β-D-ribofuranosyl)-3-aminopyrazole (870 mg) is dissolved in Toluene (10 mL) Methanimidic acid, N-cyanoethyl ester (850 mg) is added. The reaction mixture is warmed and stirred for about 6 hours. Working up is performed using toluene and bicarbonate aqueous solution. Toluene is evaporated, to give crude compound 106. Crude product is purified by CC (silica, EtAc/Hex as eluent).

NMR 1H (CDCl3, 400 MHz): 3.63 (dd, 1H, H-5'a, $J_{5'a-5'b}$=10.6 Hz, $J_{5'a-4'}$=4.3 Hz), 3.71 (dd, 1H, H-5'b, $J_{5'a-5'b}$=10.6 Hz, $J_{5'b-4'}$=4.0 Hz), 4.14 (t, 1H, H-3', J=5.1 Hz and 5.2 Hz), 4.34-4.39 (m, 2H, H-2' and H-4'), 4.51-4.66 (m, 6H, 3×CH$_2$Ph), 5.35 (d, 1H, H-1', $J_{1'-2'}$=5.8 Hz), 7.20-7.32 (m, 15H, 3×Ph), 7.97 (s, 1H, CH), 8.10 (s, 1H, CH).

Step 7: Compound 106: 4-amino-8-(2',3',5'-O-tribenzyl-β-D-ribofuranosyl) pyrazolo[1,5-a]-1,3,5-triazine (3 gr) is dissolved in DCM (50 ml) and cooled with stirring. Then, a solution of BCl$_3$ (5 ml) is added, and the solution is stirred for 1 hour. MeOH (2.5 ml) is added slowly. Solvent is evaporated under reduced pressure. Crude product is dissolved with MeOH (25 ml) and neutralized with solid NaHCO$_3$. Filtration, washing with MeOH and evaporation under reduced pressure to dryness give crude Compound 107. Crude product is purified by CC (silica, EtAc/Hex as eluent).

NMR $^1$H (MeOH, 250 MHz): 3.68 (dd, 1H, H-5'a, $J_{5'a-5'b}$=12.2 Hz, $J_{5'a-4'}$=3.5 Hz), 3.82 (dd, 1H, H-5'b, $J_{5'a-5'b}$=12.2 Hz, $J_{5'b-4'}$=3.0 Hz), 4.01-4.04 (m, 1H, H-3'), 4.16-4.21 (m, 1H, H-4'), 4.33 (dd, 1H, H-2', $J_{2'-1'}$=7.4 Hz, $J_{2'-3'}$=5.2 Hz), 4.98 (d, 1H, H-1', $J_{1'-2'}$=7.4 Hz), 8.05 (s, 1H, CH), 8.12 (s, 1H, CH).

Step 8: Compound 107: 4-amino-8-(β-D-ribofuranosyl) pyrazolo[1,5-a]-1,3,5-triazine (0.5 gr) is dissolved in pyridine (12 ml) and imidazole (0.64 gr) is added. TBDMSiCl (1.4 gr) is added and the reaction mixture is stirred for 48 h. Solvent is evaporated under reduced pressure. The crude product is extracted with DCM and water. Solvent is evaporate under reduced pressure to give crude Compound 107a. Crude product is purified by CC (silica, EtAc/PetEther as eluent). Pure compound 107a (0.49 gr) is dissolved in Pyridine (8 ml), Benzoyl chloride (0.64 gr) is added and the reaction mixture is stirred for 18 h. Water and NH$_4$OH are added, and solvent is evaporated under reduced pressure. The residue is extracted with DCM and water. Evaporation under reduced pressure to dryness to give crude Compound 107b. Crude product is purified by CC (silica, EtAc/PetEther as eluent).

Step 9: Compound 107b (1.51 gr) is dissolved in THF (33 ml), TBAF (1 M in THF, 9 ml) is added and the reaction mixture is stirred for 18 h. Solvent is evaporated under reduced pressure. Working up is performed using EtAc/water, and solvent is evaporated to dryness to give crude Compound 108. Crude product is purified by CC (silica, DCM/MeOH as eluent).

NMR $^1$H (DMSO, 250 MHz): 3.48 (dd, 1H, H-5'a, $J_{5'a-5'b}$=11.3 Hz, $J_{5'a-4'}$=4.5 Hz), 3.58 (dd, 1H, H-5'b, $J_{5'a-5'b}$=11.3 Hz, $J_{5'a-4'}$=3.9 Hz), 3.77-3.82 (m, 1H, H-4'), 3.95-4.01 (m, 1H, H-3'), 4.11-4.16 (m, 1H, H-2'), 4.85-4.90 (m, 3H, 3×OH), 4.96 (d, 1H, H-1', $J_{1'-2'}$=6.1 Hz), 7.52-7.68 (m, 3H, CH arom), 8.13 (d, 2H, CH arom), 8.22 (s, 1H, CH), 8.29 (s, 1H, CH).

Step 10: Compound 108: 4-aminobenzoyl-8-(β-D-ribofuranosyl)pyrazolo[1,5-a]-1,3,5-triazine (0.89 gr) is dissolved in dry pyridine (10 ml), a solution of DMT-Cl (0.9 gr) and the reaction mixture is stirred for 3-6 h. Solvent is evaporated under reduced pressure. Working up is performed with Hexane and water, evaporated to obtain crude product 109.

Crude product is purified by CC (silica, DCM/MeOH as eluent).

NMR $^1$H (CDCl$_3$, 400 MHz): 3.21 (dd, 1H, H5'a, $J_{5'a-5'b}$=10.1 Hz, $J_{5'a-4'}$=3.8 Hz), 3.38 (dd, 1H, H5'b, $J_{5'a-5'b}$=10.1 Hz, $J_{5'b-4'}$=3.8 Hz), 3.77 (s, 6H, OCH$_3$), 4.27-4.30 (m, 1H, H-4'), 3.37 (dd, 1H, H-3', $J_{3'-2'}$=5.4 Hz, $J_{3'-4'}$=2.3 Hz), 4.52 (dd, 1H, H-2', $J_{2'-1'}$=7.9 Hz, $J_{2'-3'}$=5.5 Hz), 5.15 (d, 1H, H-1', $J_{1'-2'}$=7.9 Hz), 6.78 (dd, 4H, CH DMT), 7.18-7.30 (m, 6H, CH arom), 7.38-7.40 (m, 2H, CH arom), 7.59 (t, 2H, CH arom), 7.67-7.69 (m, 2H, CH arom), 8.09 (sl, 2H, CH arom), 8.29 (s, 1H, CH arom), 8.51 (sl, 1H, CH arom), 10.02 (sl, 1H, NH).

Step 11: Compound 109: 4-aminobenzoyl-8-(5'-O-4,4'-dimethoxytrityl-(3-D-ribofuranosyl)pyrazolo[1,5-a]-1,3,5-triazine (0.67 gr) is dissolved in pyridine (12 ml), TBDM-SiCl (0.25 gr) is added, the reaction mixture is stirred for 6-8 h. Solvents are evaporated, working up is performed with DCM/water. Evaporation under reduced pressure to dryness gives crude Compound 110. Crude product is purified by CC (silica, DCM/MeOH/TEA as eluent).

NMR $^1$H (CDCl$_3$, 400 MHz): −0.20 (s, 3H, SiCH$_3$), -0.08 (s, 3H, SiCH$_3$), 0.77 (s, 9H, SitBu), 2.70 (d, 1H, OH, $J_{OH-3}$=3.6 Hz), 3.19 (dd, 1H, H5'a, $J_{5'a-5'b}$=10.4 Hz, $J_{5'a-4'}$=3.7 Hz), 3.42 (dd, 1H, H5'b, $J_{5'a-5'b}$=10.4 Hz, $J_{5'b-4'}$=2.8 Hz), 3.71 (s, 6H, OCH$_3$), 4.11-4.15 (m, 2H, H-4', H-3'), 4.61-4.64 (m, 1H, H-2'), 5.10 (d, 1H, H-1', $J_{1'-2'}$=6.6 Hz), 6.74 (d, 4H, CH DMT), 7.12-7.63 (m, 12H, CH arom), 8.00 (sl, 2H, CH arom), 8.18 (s, 1H, CH arom), 8.44 (sl, 1H, CH arom), 9.91 (sl, 1H, NH).

Step 12: Compound 110: 4-aminobenzoyl-8-(2'-O-tert-butyldimethylsilyl-5'-O-4,4'-dimethoxytrityl-β-D-ribofuranosyl)pyrazolo[1,5-a]-1,3,5-triazine (0.144 gr) and DCI 0.25 M, (0.68 ml) are dissolved under argon in dry, freshly distilled DCM (2 ml). PCl-reagent (0.009 ml) is then added drop wise and the mixture is stirred at RT for 1 hr. Crushed ice is added for hydrolysis and the mixture is extracted with DCM (2×15 ml), the combined organic phase washed with cold brine, dried and DCM evaporated. The crude product is purified by chromatography (eluent: pentane/EA/Et$_3$N 60/39/1) to give a white solid. Yield: 0.133 gr.

NMR $^1$H (CDCl$_3$, 400 MHz): −0.19-0.17 (d, 3H, SiCH$_3$), −0.01-0.00 (d, 3H, SiCH$_3$), 0.77 (d, 9H, SitBu), 1.13-1.18 (CH$_3$ iPr), 2.24 (t, 1H, CH$_2$CN), 2.65 (t, 1H, CH$_2$CN), 3.14-3.20 (m, 2H, H-5'), 3.46-3.60 (m, 4H, CH$_2$, CH(iPr)), 3.78 (s, 6H, OCH$_3$), 4.26-4.35 (m, 2H, H-3', H-4'), 4.68-4.71 (m, 1H, H-2'), 5.16-5.21 (m, 1H, H-1'), 6.80-6.83 (m, 4H, CH arom), 7.20-7.69 (m, 12H, CH arom), 8.11 (d, 2H, CH arom), 8.26 (d, 1H, CH arom), 8.40 (d, 1H, CH arom).

Example 3: Studying the Base Pairing Ability of the C-Nucleoside Analogue 21

18-mer oligonucleotides comprising either one or two adenine PT nucleotide analogue 21 (deoxy adenosine pyrazolotriazine derivative; $dA^{PT}$) incorporations (SEQ ID NOs. 1 and 2, respectively) were synthesized in order to study the base-pairing ability of the new $dA^{PT}$ adenine PT nucleotide analogue with thymidine. The oligonucleotide of SEQ ID No: 3 comprising a sole $dA^{PT}$ and no other purine was further synthesized in order to study its stability in acidic medium (see Table 4).

TABLE 4

Sequences of the modified (SEQ ID Nos: 1-3) and unmodified (SEQ Nos: 4-6) oligonucleotides used in this study

| SEQ ID NO: | Sequence* |
|---|---|
| 1 | 5'd-(TAC CGC GTG CAA$^{PT}$ CCC TCT) 3' |
| 2 | 5'd-(TA$^{PT}$C CGC GTG CAA$^{PT}$ CCC TCT) 3' |
| 3 | 5'd-(TTC CTC TTT CTA$^{PT}$ CCC TCT) 3' |
| 4 | 5'd-(ACA AGA GGG XTG CAC GCG GTA GGA-3' |
| 5 | 5'd-(TAC CGC GTG CAA CCC TCT) 3' |
| 6 | 5'd-(TTC CTC TTT CTA CCC TCT) 3' |

*X = A, C, G or T (in the sequence listings the X = n)
**A$^{PT}$ represents adenine PT nucleotide analogue 21

Physico-Chemical Studies

Binding Studies.

The influence of dA replacement (one or two) by the pyrazolo[1,5-a]-1,3,5-triazine derivative ($dA^{PT}$) on duplex stability was investigated by thermal denaturation studies, followed by absorption spectroscopy, using DNA duplexes obtained by mixing the modified oligonucleotides of SEQ ID NOs. 1 and 2 with the 24-mer single-stranded target DNA sequence of SEQ ID NO: 4 (X=T). The natural deoxyadenosine was also incorporated in the same positions (SEQ ID NO: 5) for comparison (duplex obtained by hybridization of the oligonucleotides of SEQ ID NOs: 4+5). Melting studies indicated that $dA^{PT}$ forms a base-pair with thymidine that contributes to duplex stability about as well as the natural A-T base pair (with melting temperature $[T_m]$=69.6° C., 69.3° C. and 69° C., respectively; FIG. 1).

Figure 2:
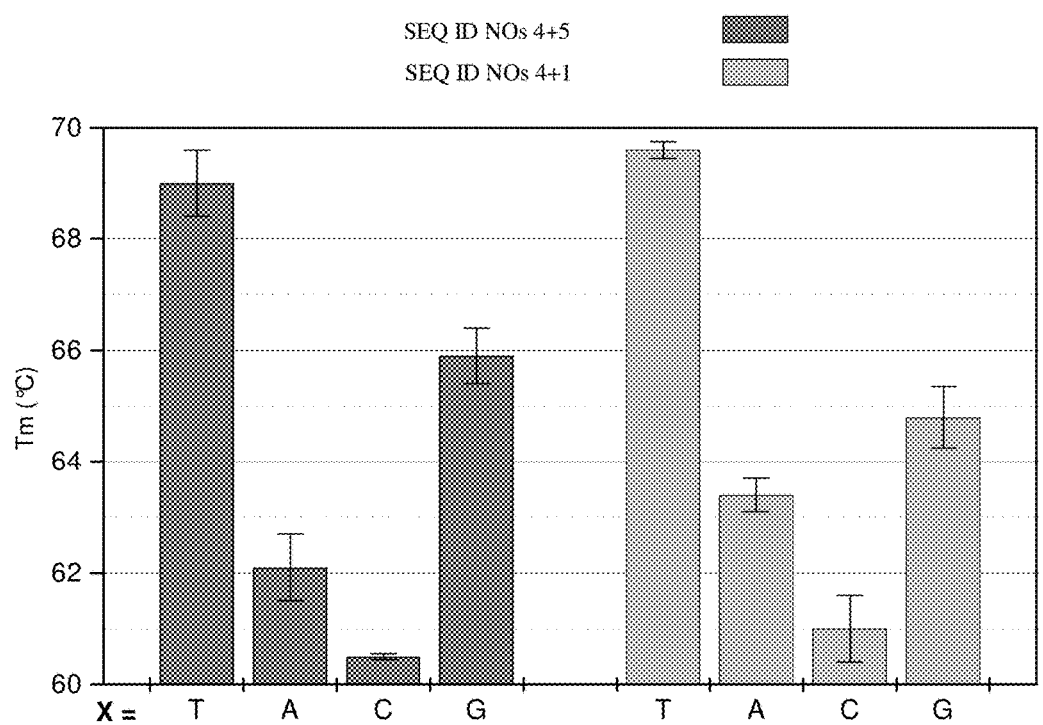
FIG. 2 shows melting temperatures for the fully matched duplexes obtained by hybridization of the oligonucleotides of SEQ ID NO: 4 (X=T)+SEQ ID NO: 5 and SEQ ID NO: 4 (X=T)+SEQ ID NO: 1; and the corresponding mismatched duplexes obtained by hybridization of the oligonucleotides of SEQ ID NO: 4 (X=A, C or G)+SEQ ID NO: 5 and SEQ ID NO: 4 (X=A, C or G)+SEQ ID NO: 1. Same conditions as for FIG. 1.

The oligonucleotide of SEQ ID NO: 1 was hybridized with the target sequence of SEQ ID NO: 4 comprising cytosine (X=C), guanine (X=G) or thymine (X=T) in the position opposite to the modified nucleoside. Melting studies indicated that $dA^{PT}$ discrimination against mismatches is at the same level as seen with deoxyadenosine, as shown in FIG. 2.

Figure 3:
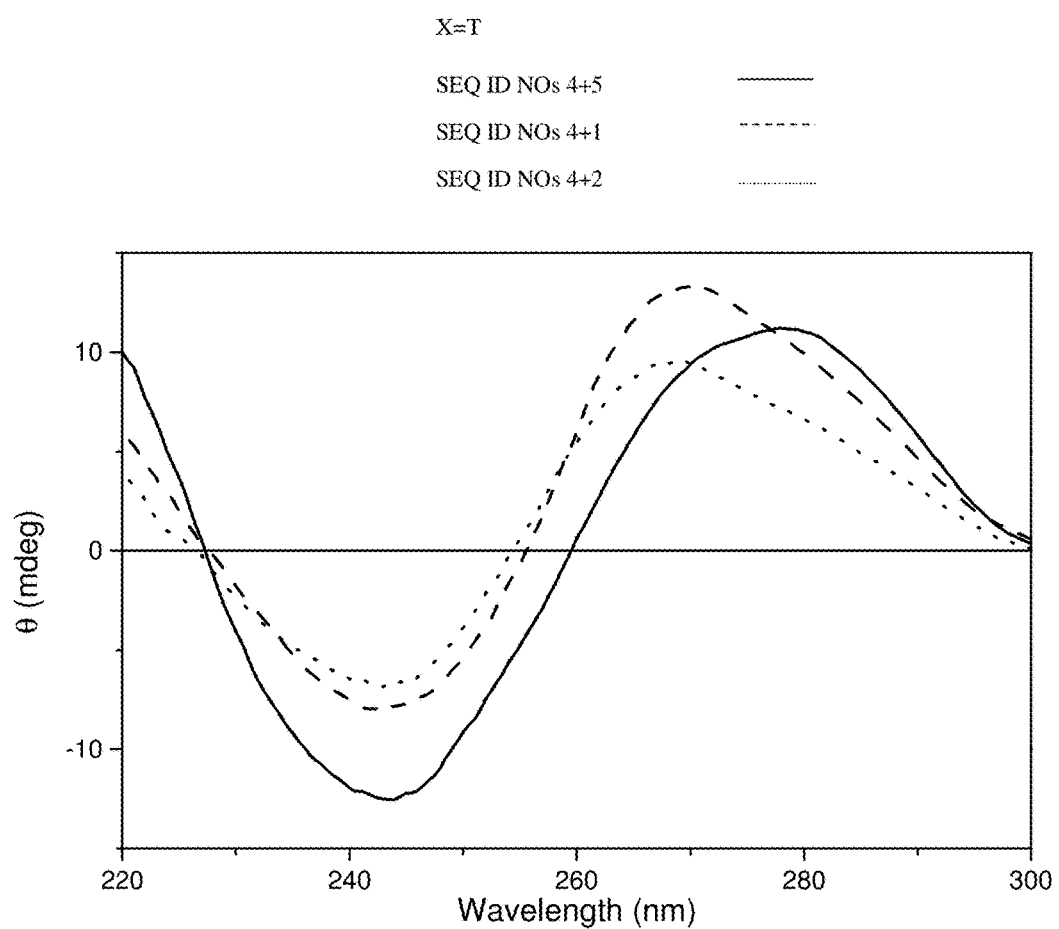
FIG. 3 shows CD spectra of the perfectly matched unmodified duplex obtained by hybridization of the oligonucleotides of SEQ ID NO: 4 (X=T)+SEQ ID NO: 5 and the modified duplexes obtained by hybridization of the oligonucleotides of SEQ ID NO: 4 (X=T)+SEQ ID NO: 1 and SEQ ID NO: 4 (X=T)+SEQ ID NO: 2 [4 μM solutions (each strand) in a 10 mM sodium phosphate, pH 7, buffer containing 150 mM NaCl and 1 mM EDTA] were recorded at 10° C. between λ=220 and 300 nm.

CD spectra of the DNA duplexes obtained from the hybridization of the oligonucleotides of SEQ ID NOs: 4+1 and 4+2, containing one or two $dA^{PT}$, respectively, were compared to that of the parent unmodified duplex obtained by hybridization of the oligonucleotides of SEQ ID NOs: 4+5. The results showed similar spectra for all three duplexes indicating that each modified one still forms a B-form duplex (FIG. 3).

Acidic Hydrolysis

In order to study the stability of the glycosidic bond of the $dA^{PT}$ described above in acidic conditions, compared with that of dA, two oligonucleotides containing a single incorporation of either $dA^{PT}$ (SEQ ID NO: 3) or the natural dA (SEQ ID NO: 6) were synthesized. Treatment of both oligonucleotides with 80% acetic acid at 65° C. for 45 hr followed by concentrated ammonium hydroxide indicated that the unmodified oligonucleotide of SEQ ID NO: 6 was fully fragmented while the oligonucleotide of SEQ ID NO: 3 containing the $dA^{PT}$ was not degraded.

Example 4: Plasmid DNA Transfection with Lipofectamine 2000®

The study described herein demonstrates the ability of an oligonucleotide comprising one or more pyrazolotriazolyl-based nucleoside analogues and designed to induce knock-down of the green fluorescent protein (GFP) expression, to be taken up as part of a tested plasmid by HELA cells expressing the GFP protein; to be transcribed by said cells; and consequently inhibit expression of GFP protein by the cells. The results presenting the percent GFP expression of said cells, indicating inhibition of GFP expression by said oligonucleotide transcript following incubation of the cells with a plasmid comprising said oligonucleotide, are compared with those obtained following incubation of such cells with a plasmid containing a scrambled sequence, as a negative control; and with a corresponding plasmid comprising a standard oligonucleotide with no pyrazolotriazolyl-based nucleoside analogues, as a positive control.

In view of the above, three sets of experiments are conducted using (i) a plasmid DNA comprising an oligonucleotide designed to induce knock-down of GFP protein expression, wherein said oligonucleotide comprises one or more pyrazolotriazolyl-based nucleoside analogues; (ii) a plasmid DNA comprising a standard non-modified oligonucleotide designed to induce knock-down of GFP protein expression (said oligonucleotide does not comprise pyrazolotriazolyl-based nucleoside analogues), as a positive control; and (iii) a plasmid DNA comprising a scrambled oligonucleotide that cannot induce knock down of GFP protein expression, as a negative control.

One µg plasmid DNA is diluted in 100 µl OPTI-MEM® and mixed gently. In addition, different solutions containing 2, 4, 6, 8 or 10 µl of Lipofectamine 2000® in 100 µl OPTI-MEM® are prepared, mixed gently and incubated for 5 min at room temperature.

The DNA plasmid and a Lipofectamine 2000® reagent prepared are combined and mixed gently, and are then incubated at room temperature. These mixes are then added to HELA cells in a an appropriate medium and incubated for 24 hrs, following which the green fluorescent protein (GFP) fluorescence intensity is analyzed by FACS, looking for percent of GFP-positive cells. After incubation of the tested plasmid, we expect observing a decrease in GFP-positive cells.

REFERENCES

Arai, I., Daves, G. D., *J. Am. Chem. Soc.,* 1978, 100, 287
Cheng, J. C. Y., Hacksell, U., Daves, G. D. Jr., *J. Org. Chem.,* 1986, 51, 3093-3098
Chu, C. K., Watanabe, K. A., Fox, J. J., *J. Heterocyclic Chem.,* 1980, 17, 1435-1439
Daves, G. D., *Acc. Chem. Res.,* 1990, 23, 201-206
Dellinger, D. J., Betley, J. R., Wyrzykiewicz, T. K., Caruthers, M. H., Synthesis of DNA using a new two-step cycle, *Methods Mol Biol.,* 2005, 288, 1-16
Hartsel, S. A., Kitchen, D. E., Scaringe S. A., Marshall W. S., RNA oligonucleotide synthesis via 5'-silyl-2'-orthoester chemistry, *Methods Mol Biol.,* 2005, 288, 33-50
Hayakawa, Y., Wakabayashi, S., Kato, H., Noyori, R., *J. Am. Chem. Soc.,* 1990, 112, 1691-1696

Il'icheva et al., *Russian Journal of Bioorganic Chemistry*, 2005, 31, 439-452

Larsen, E., Jorgensen, P. T., Sofan, M. A., Pedersen, E. B., *Synthesis*, 1994, 1037-1038

Liang, C., Ma, T., Cooperwood, J. S., Du, j., Chu, C., *Carbohydrate Research*, 1997, 303, 33-88

Mathieu, R., Schmitt, M., Bourguignon, J. J., *Tetrahedron Lett.*, 2006, 47, 5099-5103

Miller, R. L., Adamczyk, D. L., Miller, W. H., Koszalka, G. W., Rideout, J. L., Beacham, L. M., Chao, E. Y., Haggerty, J. J., Krenitsky, T. A., Elion, G. B., *The Journal of Biological Chemistry*, 1979, 254, 2346-2352

Otter, B. A., Klein, R. S., Nucleosides & Nucleotides, 1996, 15(1-3), 793-807

Pedroso, E., Escaja, N., Frieden, M., Grandas, A., Solid-phase synthesis of circular oligonucleotides, *Methods Mol Biol.*, 2005, 288, 106-126

Raboisson, P., Baurand, A., Cazenave, J. P., Gachet, C., Schultz, D., Spiess, B., Bourguignon, J-J., *J. Org. Chem.*, 2002, 67, 8063-8071

Raboisson, P., Schultz, D., Muller, C., Reimund, J. M., Pinna, G., Mathieu, R, Bernard, P., Do, Q. T., DesJarlais, R. L., Justiano, H., Lugnier, C., Bourguignon, J. J., *Eur. J Med. Chem.*, 2008, 43, 816-829

Schaller, H., Weimann, G., Lerch, B., Khorana, H. G., *J. Am. Chem. Soc.*, 1963, 85, 3821-3827

Sproat, B. S., RNA synthesis using 2'-O-(tert-butyldimethylsilyl) protection, *Methods Mol Biol.*, 2005, 288, 17-32

Stambasky, J., Hocek, M., Kocovsky, P., *Chem. Rev.*, 2009, 109, 6729-6764

Stawinski, J., Stromberg, R., Di- and oligonucleotide synthesis using H-phosphonate chemistry, *Methods Mol Biol.*, 2005, 288, 81-100

Tam, S. Y. K., Hwang, J. S., De Las Heras, F. G., Klein, R. S., Fox, J. J., *Journal of Heterocyclic Chemistry*, 1976, 13, 1305-1308

Tam, S. Y. K., Klein, R. S., Wempen, I., Fox, J. J., *J. Org. Chem.*, 1979, 44, 4547-4553

Wellington, K. W., Benner, S. A., *Nucleosides, Nucleotides and Nucleic Acids*, 2006, 25, 1309-1333

Zarubin, Y. P., Il'icheva, I. A., Purygin, P. P., Florent'ev, V. L., *Russian Journal of Bioorganic Chemistry*, 2002, 28, 404-411

Zarubin et al., *Vestnic Samarskogo Gosudarstvennogo Universiteta*, Estestvennonauchnaya Serya, 2003, (Spec.), 152-173

Zhang, H. C., Brakta, M., Daves, G. D., *Nucleosides & Nucleotides*, 1995, 14, 105-116

---

The invention claimed is:

1. A 9-adeninyl or 9-guaninyl PT nucleoside or nucleotide analogue of the general formula I:

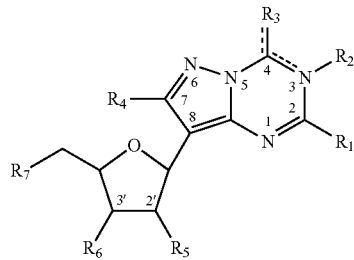

wherein $R_1$ and $R_4$ each independently is selected from H, halogen, —CN, —SCN, —NO$_2$, —O-hydrocarbyl, —S-hydrocarbyl, —CO—H, —CO-hydrocarbyl, —NR$_8$R$_9$, heteroaryl, and hydrocarbyl optionally substituted by one or more groups each independently is halogen, —CN, —SCN, and —NO$_2$, wherein R$_8$ and R$_9$ are each independently H, hydrocarbyl, benzoyl, or an amine protecting group, provided that at least one of R$_8$ and R$_9$ is not H; or R$_8$ or R$_9$ together with the nitrogen atom to which they are attached form a saturated or unsaturated heterocyclic ring optionally containing 1-2 further heteroatoms selected from oxygen, nitrogen and sulfur;

$R_2$ is H or absent;

$R_3$ is O or —NR$_{10}$R$_{10'}$, wherein R$_{10}$ and R$_{10'}$ are each independently H, hydrocarbyl, —CO-hydrocarbyl, or an amine protecting group, provided that at least one of R$_{10}$ and R$_{10'}$ is not H;

provided that at least one of R$_1$ and R$_3$ is —NR$_8$benzoyl or —NR$_{10}$benzoyl, respectively;

wherein $R_5$ is halogen or —OR$_{11}$;

$R_6$ is —OR$_{11}$;

$R_7$ is —OR$_{11}$, or a phosphate moiety;

wherein each R$_{11}$ is independently selected from (C$_1$-C$_8$)alkyl, (C$_1$-C$_8$)alkylene-OR$_{12}$, (C$_1$-C$_8$)alkylene-SR$_{12}$, (C$_1$-C$_8$)alkylene-NR$_{12}$R$_{13}$, a hydroxyl protecting group, or a phosphoramidite moiety of the formula —P(OR$_{14}$)NR$_{15}$R$_{16}$, wherein R$_{14}$ is or cyano-(C$_1$-C$_8$)alkyl, and R$_{15}$ and R$_{16}$ each independently is (C$_1$-C$_8$)alkyl;

$R_{12}$ and $R_{13}$ each independently is H or (C$_1$-C$_8$)alkyl, provided that at least one of R$_{12}$ and R$_{13}$ is not H; and the dotted line represents a potential double bond between the carbon atom at position 4 and either the nitrogen atom at position 3 or the radical $R_3$, provided that, when $R_2$ is H, there is a double bond between the carbon atom at position 4 and $R_3$, and when $R_2$ is absent, there is a double bond between the carbon atom at position 4 and the nitrogen atom at position 3 and $R_3$ is $NR_{10}R_{10'}$; with the proviso that only one of $R_5$, $R_6$ and $R_7$ is a phosphoramidite moiety.

2. The 9-adeninyl or 9-guaninyl PT nucleoside or nucleotide analogue or of claim 1, wherein
  (i) $R_5$ is —$OR_{11}$, wherein $R_{11}$ is $(C_1-C_8)$alkyl, $(C_1-C_8)$ alkylene-$OR_{12}$, $(C_1-C_8)$alkylene-$SR_{12}$, $(C_1-C_8)$alkylene-$NR_{12}R_{13}$, or a hydroxyl protecting group; and $R_6$ is —$OR_{11}$, wherein $R_{11}$ is a phosphoramidite moiety of the formula —$P(OR_{14})NR_{15}R_{16}$, provided that at least one of $R_{12}$ and $R_{13}$ is not H; or
  (ii) $R_5$ is —$OR_{11}$, wherein $R_{11}$ is a phosphoramidite moiety of the formula —$P(OR_{14})NR_{15}R_{16}$; and $R_6$ is —$OR_{11}$, wherein $R_{11}$ is $(C_1-C_8)$alkyl, $(C_1-C_8)$alkylene-$OR_{12}$, $(C_1-C_8)$alkylene-$SR_{12}$, $(C_1-C_8)$alkylene-$NR_{12}R_{13}$, or a hydroxyl protecting group, provided that at least one of $R_{12}$ and $R_{13}$ is not H.

3. The nucleoside or nucleotide analogue according to claim 1, wherein the nucleoside or nucleotide analogue is a 9-adeninyl PT nucleoside or nucleotide analogue, and wherein $R_1$ and $R_4$ each independently is H, halogen, $(C_1-C_2)$alkyl, —O—$(C_1-C_2)$alkyl, —S—$(C_1-C_2)$alkyl, —CO—H, —CO—$(C_1-C_2)$alkyl, or —$NR_8R_9$, wherein $R_8$ and $R_9$ are each independently H, $(C_1-C_2)$alkyl, benzoyl, or an amine protecting group; $R_2$ is absent; $R_3$ is —$NR_{10}R_{10'}$, wherein $R_{10}$ and $R_{10'}$ are each independently H, benzoyl, or an amine protecting group; provided that at least one of $R_8$, $R_9$, $R_{10}$ and $R_{10'}$ is benzoyl provided that at least one of $R_8$ and $R_9$ is not H and provided that at least one of $R_{10}$ and $R_{10'}$ is not H; $R_5$ is halogen, or —$OR_{11}$; $R_6$ is —$OR_{11}$; $R_7$ is —$OR_{11}$, or a phosphate moiety; and $R_{11}$ each independently is $(C_1-C_4)$alkyl, $(C_1-C_4)$alkylene-OH, $(C_1-C_4)$alkylene-$OCH_3$, $(C_1-C_4)$alkylene-SH, $(C_1-C_4)$alkylene-$SCH_3$, $(C_1-C_4)$alkylene-$NH_2$, a hydroxyl protecting group, or —P(O-cyanoethyl)N(i-propyl)$_2$; with the proviso that only one of $R_5$, $R_6$ and $R_7$ is a phosphoramidite moiety.

4. The nucleoside or nucleotide analogue of claim 3, wherein:
  (i) $R_1$ and $R_4$ are H; $R_2$ is absent; $R_3$ is —$NR_{10}R_{10'}$; $R_5$ is —$OCH_3$; $R_6$ is —$OR_{11}$, wherein $R_{11}$ is —P(O-cyanoethyl)N(i-propyl)$_2$; $R_7$ is —ODMT; and $R_{10}$ and $R_{10'}$ are each independently H or benzoyl, wherein at least one of $R_{10}$ and $R_{10'}$ is benzoyl and only one of $R_{10}$ and $R_{10'}$ is H;
  (ii) $R_1$ and $R_4$ are H; $R_2$ is absent; $R_3$ is —$NR_{10}R_{10'}$; $R_5$ is —$OR_{11}$, wherein $R_{11}$ is —P(O-cyanoethyl)N(i-propyl)$_2$; $R_6$ is —$OCH_3$; $R_7$ is —ODMT; and $R_{10}$ and $R_{10'}$ are each independently H or benzoyl, wherein at least one of $R_{10}$ and $R_{10'}$ is benzoyl and only one of $R_{10}$ and $R_{10'}$ is H;
  (iii) $R_1$ and $R_4$ are H; $R_2$ is absent; $R_3$ is —$NR_{10}R_{10'}$; $R_5$ is —$O(CH_2)_2$—$OCH_3$; $R_6$ is —$OR_{11}$, wherein $R_{11}$ is —P(O-cyanoethyl)N(i-propyl)$_2$; $R_7$ is —ODMT; and $R_{10}$ and $R_{10'}$ are each independently H or benzoyl, wherein at least one of $R_{10}$ and $R_{10'}$ is benzoyl and only one of $R_{10}$ and $R_{10'}$ is H;
  (iv) $R_1$ and $R_4$ are H; $R_2$ is absent; $R_3$ is —$NR_{10}R_{10'}$; $R_5$ is —$OR_{11}$, wherein $R_{11}$ is —P(O-cyanoethyl)N(i-propyl)$_2$; $R_6$ is —$O(CH_2)_2$—$OCH_3$; $R_7$ is —ODMT; and $R_{10}$ and $R_{10'}$ are each independently H or benzoyl, wherein at least one of $R_{10}$ and $R_{10'}$ is benzoyl and only one of $R_{10}$ and $R_{10'}$ is H.

5. The nucleoside or nucleotide analogue according to claim 1, wherein the nucleoside or nucleotide analogue is a 9-guaninyl PT nucleoside or nucleotide analogue, and wherein $R_1$ is —$NR_8R_9$, wherein $R_8$ and $R_9$ are each independently H, benzoyl or an amine protecting group, provided that at least one of $R_8$ and $R_9$ is not H; $R_2$ is H; $R_3$ is O; $R_4$ is H, halogen, $(C_1-C_2)$alkyl, —O—$(C_1-C_2)$alkyl, —S—$(C_1-C_2)$alkyl, —CO—H, —CO—$(C_1-C_2)$alkyl, or —$NR_8R_9$, wherein $R_8$ and $R_9$ are each independently H, benzoyl, $(C_1-C_2)$alkyl or an amine protecting group, provided that at least one of $R_8$ and $R_9$ is not H; $R_5$ is halogen, or —$OR_{11}$; $R_6$ is —$OR_{11}$; $R_7$ is —$OR_{11}$, or a phosphate moiety; and $R_{11}$ each independently is $(C_1-C_4)$ alkyl, $(C_1-C_4)$ alkylene-OH, $(C_1-C_4)$ alkylene-$OCH_3$, $(C_1-C_4)$alkylene-SH, $(C_1-C_4)$alkylene-$SCH_3$, $(C_1-C_4)$alkylene-$NH_2$, a hydroxyl protecting group, or —P(O-cyanoethyl)N(i-propyl)$_2$, provided that at least one of $R_8$ and $R_9$ is benzoyl and that at least one of $R_8$ and $R_9$ is not H and provided that at least one of $R_6$ and $R_7$ is not a phosphoramidite moiety; with the proviso that only one of $R_5$, $R_6$ and $R_7$ is a phosphoramidite moiety.

6. The nucleoside or nucleotide analogue of claim 5, wherein:
  (i) $R_1$ is —$NHR_9$; $R_2$ is H; $R_3$ is O; $R_4$ is H; $R_5$ is —$OCH_3$; $R_6$ is —$OR_{11}$, wherein $R_{11}$ is —P(O-cyanoethyl)N(i-propyl)$_2$; $R_7$ is —ODMT; and $R_9$ is benzoyl;
  (ii) $R_1$ is —$NHR_9$; $R_2$ is H; $R_3$ is O; $R_4$ is H; $R_5$ is —$OR_{11}$, wherein $R_{11}$ is —P(O-cyanoethyl)N(i-propyl)$_2$; $R_6$ is —$OCH_3$; $R_7$ is —ODMT; and $R_9$ is benzoyl;
  (iii) $R_1$ is —$NHR_9$; $R_2$ is H; $R_3$ is O; $R_4$ is H; $R_5$ is —$O(CH_2)_2$—$OCH_3$; $R_6$ is —$OR_{11}$, wherein $R_{11}$ is —P(O-cyanoethyl)N(i-propyl)$_2$; $R_7$ is —ODMT; and $R_9$ is benzoyl;
  (iv) $R_1$ is —$NHR_9$; $R_2$ is H; $R_3$ is O; $R_4$ is H; $R_5$ is —$OR_{11}$, wherein $R_{11}$ is —P(O-cyanoethyl)N(i-propyl)$_2$; $R_6$ is —$O(CH_2)_2$—$OCH_3$; $R_7$ is —ODMT; and $R_9$ is benzoyl.

* * * * *